(12) United States Patent
Vetrovec et al.

(10) Patent No.: US 7,486,250 B2
(45) Date of Patent: Feb. 3, 2009

(54) COMPOSITE DIPOLE ARRAY

(75) Inventors: Jan Vetrovec, Thousand Oaks, CA (US); Sandor Holly, Woodland Hills, CA (US)

(73) Assignee: The Boeing Company, Chicago, IL (US)

( * ) Notice: Subject to any disclaimer, the term of this patent is extended or adjusted under 35 U.S.C. 154(b) by 159 days.

(21) Appl. No.: 11/057,937

(22) Filed: Feb. 15, 2005

(65) Prior Publication Data
US 2005/0200550 A1    Sep. 15, 2005

Related U.S. Application Data

(63) Continuation-in-part of application No. 10/780,525, filed on Feb. 16, 2004, now Pat. No. 6,999,041, and a continuation-in-part of application No. 10/780,520, filed on Feb. 16, 2004, now Pat. No. 6,950,076, and a continuation-in-part of application No. 10/780,536, filed on Feb. 16, 2004, now Pat. No. 7,009,575, and a continuation-in-part of application No. 10/780,535, filed on Feb. 16, 2004, now Pat. No. 6,943,742.

(51) Int. Cl.
*H01Q 9/16* (2006.01)
(52) U.S. Cl. .................. 343/820; 343/795; 343/814; 343/824
(58) Field of Classification Search ............... 343/793, 343/795, 802, 814, 816, 820, 822, 824
See application file for complete search history.

(56) References Cited

U.S. PATENT DOCUMENTS

| | | | |
|---|---|---|---|
| 3,348,093 A | | 10/1967 | Holly |
| 3,852,755 A | * | 12/1974 | Works et al. ............. 343/701 |
| 3,919,638 A | * | 11/1975 | Belden, Jr. .............. 324/95 |
| 4,634,968 A | * | 1/1987 | Aslan ................. 324/95 |
| 4,638,813 A | * | 1/1987 | Turner ................. 607/154 |

(Continued)

FOREIGN PATENT DOCUMENTS

EP    01101006    4/1989

(Continued)

OTHER PUBLICATIONS

Park et al., A Novel Lateral Field Emitter Triode with Insitu Vacuum Encapulation, International Electron Devices Meeting, 1996 (4 pages).

(Continued)

*Primary Examiner*—Tho G Phan
(74) *Attorney, Agent, or Firm*—MacPherson Kwok Chen & Heid LLP; Greg J. Michelson

(57) ABSTRACT

Methods and systems for generating and imaging THz electromagnetic radiation using a composite dipole array made up of novel structures of non-linear dipole strings with dual frequency resonances for frequency up conversion and frequency down conversion are disclosed. THz electromagnetic radiation resulting from the frequency down conversion process can be used as an illumination source for imaging, as a carrier for communications, or as an energy source for spectroscopy, for example. Optical electromagnetic radiation resulting from the frequency up conversion process can be used to form images from THz electromagnetic radiation for contraband detection, guidance systems, and medical applications, for example.

34 Claims, 12 Drawing Sheets

U.S. PATENT DOCUMENTS

| | | | |
|---|---|---|---|
| 5,030,962 A | 7/1991 | Rees | |
| 5,233,263 A | 8/1993 | Cronin | |
| 5,308,439 A | 5/1994 | Cronin | |
| 5,420,595 A | 5/1995 | Zhang et al. | |
| 5,856,803 A | 1/1999 | Pevler | |
| 6,492,957 B2 * | 12/2002 | Carillo et al. | 343/841 |
| 6,864,825 B2 | 3/2005 | Holly | |
| 6,943,742 B2 | 9/2005 | Holly | |
| 6,950,076 B2 | 9/2005 | Holly | |
| 6,999,041 B2 | 2/2006 | Holly | |
| 7,009,575 B2 | 3/2006 | Holly | |
| 7,142,147 B2 | 11/2006 | Holly | |
| 2002/0075189 A1 * | 6/2002 | Carillo et al. | 343/702 |
| 2004/0008149 A1 * | 1/2004 | Killen et al. | 343/795 |
| 2005/0088358 A1 | 4/2005 | Larry et al. | |

FOREIGN PATENT DOCUMENTS

| | | |
|---|---|---|
| GB | 2121612 | 12/1983 |
| GB | 2121612 A | 12/1983 |
| JP | 01-101006 | 4/1989 |
| JP | 2006/211637 | 8/2006 |
| WO | WO 03/019738 A1 | 3/2003 |
| WO | WO 2005/093904 | 10/2005 |
| WO | WO2006/088802 A2 | 8/2006 |
| WO | PCT/US2008/061106 | 4/2008 |

OTHER PUBLICATIONS

Park et al., Lateral Field Emission Diodes Using SIMO Wafer, IEEE Transactions on Electron Devices, vol. 44, No. 6, Jun. 1997 (4 pages).

Milanovic et al., Micromatching Technology for Lateral Field Emission Devices, IEEE Transactions on Electron Devices, vol. 48, No. 1, Jan. 2001 (8 pages).

Peter H. Siegel, Terahertz Technology, IEEE Transactions on Microwave Theory and Techniques, Mar. 2002, pp. 910-928, vol. 50, No. 3.

Peter H. Siegel, THz Technology; An Overview, International Journal of High Speed Electronics and Systems, 2003, pp. 1-44, vol. 13, No. 2, World Scientific Publishing Company, USA.

Raman et al., A W-Band Dielectric-Lens-Based Integrated Monopulse Radar Receiver, IEEE Transactions on Microwave Theory and Techniques, Dec. 1998, pp. 2308-2316, vol. 46, No. 12.

Filipovic et al., Off-Axis Properties of Silicon and Quartz Dielectric Lens Antennas, IEEE Transactions on Antennas and Propagation, May 1997, pp. 760-766, vol. 45, No. 5.

* cited by examiner

COMPOSITE DIPOLE ARRAY

RELATED APPLICATIONS

This patent application is a continuation-in-part patent application of: U.S. Ser. No. 10/780,525 filed on Feb. 16, 2004 now U.S. Pat. No. 6,999,041 and entitled DUAL FREQUENCY ANTENNAS AND ASSOCIATED DOWN-CONVERSION METHOD; U.S. Ser. No. 10/780,520 filed on Feb. 16, 2004 now U.S. Pat. No. 6,950,076 and entitled TWO-DIMENSIONAL DUAL-FREQUENCY ANTENNA AND ASSOCIATED DOWN-CONVERSION METHOD; U.S. Ser. No. 10/780,536 filed on Feb. 16, 2004 now U.S. Pat. No. 7,009,575 and entitled HIGH-FREQUENCY TWO-DIMENSIONAL ANTENNA AND ASSOCIATED DOWN-CONVERSION METHOD; and U.S. Ser. No. 10/780,535 filed on Feb. 16, 2004 now U.S. Pat. No. 6,943,742 and entitled FOCAL PLANE ARRAY FOR THZ IMAGER AND ASSOCIATED METHODS, the entire contents of all of which are hereby expressly incorporated by reference.

TECHNICAL FIELD

The present invention relates generally to antennas and, more particularly, to a composite dipole array for the generation and/or detection of electromagnetic radiation.

BACKGROUND

A Terahertz (THz) is a unit of frequency equal to $10^{12}$ hertz. THz electromagnetic radiation forms a large portion of the electromagnetic spectrum between the infrared and microwave regions. THz electromagnetic radiation is generally defined as covering frequencies from about 0.3 THz to about 30 THz. This corresponds to the range of wavelengths from about 1.0 mm to about 0.01 mm and is sometimes referred to as the sub-millimeter and/or far-infrared region of the electromagnetic spectrum. By way of comparison, visible light covers the frequency range of 428 THz to 750 THz, corresponding to wavelengths from 0.4 micron to 0.7 micron. Thus, THz electromagnetic radiation is in a previously much neglected range of frequencies between optical and radio waves.

THz electromagnetic radiation has interesting properties because its wavelengths are long enough to pass through some objects that are opaque to visible and IR light and are also short enough to be manipulated by conventional optical techniques. Thus, THz electromagnetic radiation can be used for the imaging of hidden objects. It is a particularly attractive means of detection because it can determine the composition, size, and shape of a variety of different substances.

The potential uses of THz electromagnetic radiation in various fields are presently being investigated. Specific applications include remote sensing, short range covert communications, compact radar ranging systems, inter-satellite communication links, testing of integrated circuits, and even medical imaging and treatment. In the field of medical imaging, for example, tumors and other pathologies may be identified and characterized. THz electromagnetic radiation may even find applications in a variety of other areas, including atmospheric sensing and upper atmospheric imagery.

Research into the potential use of THz electromagnetic radiation for the detection and characterization of contraband, such as chemicals (including illegal drugs, explosives, and toxic substances), biological agents (including aerosols) and concealed weapons, is being stimulated by law enforcement and homeland security concerns. By using THz electromagnetic radiation, drugs, explosives, and pathogens can be identified in parcels before they are opened. Concealed guns and knives can be observed on people. Even mines in minefields can potentially be located.

Further, the use of ambient THz electromagnetic radiation facilitates standoff detection of weapons and explosives. Standoff detection is particularly useful in determining whether a threat exists prior to the item or person posing the threat actually entering a sensitive area. That is, the threat can be identified before there is an opportunity to do the intended harm. For example, a THz electromagnetic radiation imaging system can be employed at the gate to a military base. If a threat is perceived, then the person posing the potential threat can be denied entry.

THz time-domain spectroscopy and related THz technologies promise to be of great benefit for military and civilian uses, because they offer innovative imaging and sensing technologies that can provide information not available through such conventional methods as microwave and x-ray. Spectral fingerprints can facilitate the identification of suspicious items. The resolution of such spectra can be impressive. Not only can the type of explosive, drug, or pathogen be determined, but many times the factory where the substance was manufactured can be identified, as well. Thus, the potential forensic benefits are clear.

Compared to the relatively well-understood science and technology at microwave and optical frequencies, THz science and technology is in its infancy. This is largely due to the inadequate power of available contemporary THz sources and the limited resolution of contemporary THz imaging receivers.

The use of THz electromagnetic radiation in such applications is particularly attractive because, in many instance, it can be used passively. That is, THz electromagnetic radiation can be viewed without actively illuminating the subject. Other forms of imaging, such as those using x-ray and gamma ray backscatter, require that the subject be illuminated so as to provide the necessary radiation. Such illumination tends to pose some degree of health risks to human subjects and imaging equipment operators. However, in many instances sufficient THz electromagnetic radiation is generally present in the ambient environment to facilitate imaging. Thus, illumination is not always necessary for THz imaging. The elimination of a source of radiation by using ambient radiation both reduces costs and eliminates health concerns. It is also useful in covert applications.

In industrial applications, such as manufacturing and quality control, the use of an active source may be less objectionable. In such settings, provision for shielding can more readily be made. Further, in industrial settings the cost and space required for a source tend to be less problematic. Imaging can potentially be accomplished in either a transmission mode or a reflection mode of operation. In the transmission mode, the radiation source is on the opposite side of the subject with respect to the detection device and the radiation is transmitted through the subject to detect substances therein. In the reflection mode, the radiation source is on the same side of the subject with respect to the detection device and the radiation is reflected by substances within the subject.

Sensors for detecting THz electromagnetic radiation are presently being developed. Although prices are expect to decrease as development proceeds and as the sensors are produced in volume, the cost of contemporary sensors is high.

Another problem associated with the use of THz electromagnetic radiation is that contemporary THz electromagnetic radiation sources with suitable output power levels are undesirably large, heavy, and costly. The only way to generate THz electromagnetic radiation with average power over a watt, according to contemporary practice, is to use an accelerator, such as a 15 MeV synchrotron. As those skilled in the art will appreciate, such THz electromagnetic radiation sources are very large and very expensive. Even in industrial environments, it is generally desirable to reduce the size and cost of equipment.

In view of the foregoing, it is desirable to provide a source of THz electromagnetic radiation with output power levels of a few hundred milliwatts and higher that is smaller in size and less costly than contemporary sources. It is also desirable to provide a way to more readily facilitate the imaging in the THz frequency range of the electromagnetic spectrum.

SUMMARY

Systems and methods are disclosed herein for generating THz electromagnetic radiation and for imaging in the THz frequency range. For example, in accordance with an embodiment of the present invention, two laser beams interact with a composite dipole array (CDA) to frequency down convert to a beat (difference) frequency so as to provide THz electromagnetic radiation. In accordance with another embodiment of the present invention, a laser beam and image bearing THz electromagnetic radiation interact with a composite dipole array to frequency up convert the THz electromagnetic radiation to an optical frequency, the intensity distribution of which is subsequently imaged conventionally.

More specifically, in accordance with one embodiment of the present invention, a pair of infrared ring type optical resonator lasers have beams that are incident upon a common portion of a composite dipole array. The composite dipole array interacts with the two IR beams from the two lasers and re-radiates energy at the difference THz frequencies.

In accordance with another embodiment of the present invention, a beam from an infrared ring type optical resonator laser and image bearing THz electromagnetic radiation are incident upon a composite dipole array, such as upon opposite sides thereof. The composite dipole array interacts with the laser beam and the THz electromagnetic radiation and re-radiates image bearing electromagnetic radiation at optical frequencies (e.g., infrared frequencies).

The present invention provides methods and systems for generating and imaging THz electromagnetic radiation for a variety of applications such as remote sensing, short range covert communications, compact radar ranging systems, inter-satellite communication links, testing integrated circuits, and even medical imaging and treatment.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION

Figure 1:
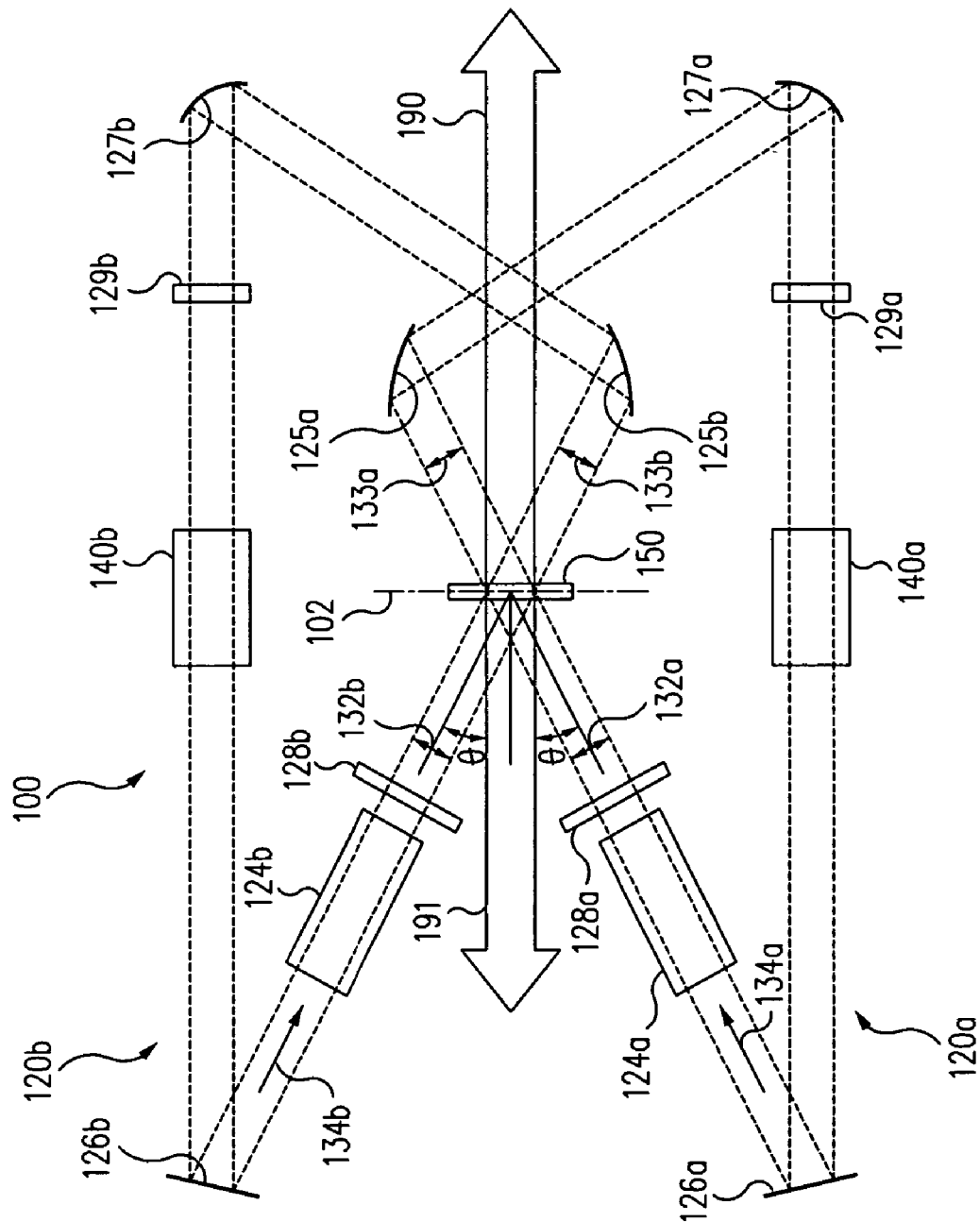
FIG. 1 shows a block diagram illustrating a THz radiation generator in accordance with an exemplary embodiment of the present invention.

One aspect of the present invention comprises a system and method for the generation of narrowband, high-power, THz electromagnetic radiation. Another aspect of the present invention comprises a system and method for the high-resolution detection of THz electromagnetic radiation. As disclosed herein, both the generation and detection of THz electromagnetic radiation utilizes a hybrid frequency conversion (HFC) technique. The HFC technique takes advantage of the interaction of electromagnetic radiation with miniature dipole antennas, miniature resonant circuits—all on the micron and submicron (nano) scale together with solid-state electronics to enable frequency mixing for down conversion from optical to THz frequencies to provide a THz electromagnetic radiation source and/or up-conversion from THz to optical frequencies to provide an imager at THz frequencies. Unlike contemporary techniques for the generation and detection of THz electromagnetic radiation, HFC provides high efficiency, which is a key factor in the development of compact, lightweight, and portable THz imaging systems.

According to one aspect of the present invention, the hybrid Frequency Conversion (HFC) is performed using a composite dipole array (CDA), which facilitates frequency mixing in the optical and THz regions. As discussed in detail below, the composite dipole array is a two-dimensional array of one-dimensional dipole strings, wherein each of the one-dimensional dipole arrays defines a macro-dipole antenna. A one-dimensional dipole array or macro-dipole antenna is a one-dimensional array of adjacent (end-to-end) micro-dipole antennas. Adjacent micro-dipole antennas are electrically interconnected with non-linear resonant circuits which facilitate efficient frequency conversion.

As used herein, macro-dipole antennas include antennas that are comprised of connected smaller micro-dipole antennas, and micro-dipole antennas cooperate to define the larger macro-dipole antennas. Thus, the terms macro and micro can refer to the relative size of the antennas with respect to one another and the way that these antennas cooperate to define or be defined by one another.

According to one aspect of the present invention, energy is extracted from two spatially overlapping $CO_2$ laser beams that have been outcoupled from their respective laser resonator cavities. The beams overlap upon a composite dipole array. The composite dipole array includes micro-dipoles formed of a conductor, such as metal or metal alloy, having high electric conductivity. As discussed in detail below, the composite dipole array comprises suitable linear and non-linear lumped or distributed circuit elements, e.g., diodes, capacitors, inductors and resistors.

The combined physical area of the micro-dipoles presented to the incident laser beams is only a small fraction of the composite dipole array surface illuminated by the laser beams. Thus, the composite dipole array can be described in general as being optically thin unless the individual microdipoles are made to resonate at the frequency of the incident laser. The generation of THz electromagnetic radiation is facilitated by the coupling of $CO_2$ laser energy into the micro-dipoles. When the $CO_2$ laser frequency is not close to the resonant frequency of the micro-dipoles, less than 1% of the incident $CO_2$ laser light is absorbed by the micro-dipoles. However, when the $CO_2$ laser frequency is tuned to the resonance frequency of the micro-dipoles, a significant portion of the incident $CO_2$ laser radiation is coupled into the micro-dipoles, efficiently converted to dipole currents, and then converted into THz electromagnetic radiation. This THz radiation is extracted in the form of a collimated beam.

That portion of the incident $CO_2$ energy not extracted by the dipoles passes though the composite dipole array and would be lost. This loss limits the conversion efficiency to generally less than 20%. According to one aspect, the present invention reduces this loss to as little as few percent by recovering most of the $CO_2$ laser energy not extracted by the composite dipole array in one pass and recycles it. As a result, conversion efficiency is greatly improved compared to systems without such recycling.

FIG. 1 shows a THz electromagnetic radiation generator 100 in accordance with one exemplary embodiment of the present invention. THz electromagnetic radiation generator 100 comprises two lasers 120a and 120b and a composite dipole array 150. The composite dipole array 150 is substantially contained within a plane 102 that is perpendicular to the plane of FIG. 251. Optical resonators used by said lasers 120a and 120b can be of the ring type (also known as traveling wave type) formed by a gain medium 124a and reflectors 125a, 126a, and 127a for laser 120a and formed by gain medium 124b and reflectors 125b, 126b, and 127b for laser 120b.

Reflectors 126a and 126b can be either flat mirrors or diffraction gratings. Reflectors 125a, 125b, 127a, and 127b can be curved (e.g., parabolic) mirrors.

Lasers 120a and 120b generate laser beams 132a and 132b at laser frequencies $f_1$ and $f_2$, respectively. A predetermined frequency difference $f_1$-$f_2$ is equal to the frequency $f_3$ of the desired THz output. Laser beams 132a and 132b can each be incident upon composite dipole array 150 at an angle θ with respect to a normal of plane 102 of composite dipole array 150 and at an angle 2θ with respect to each other. Additionally, the two laser beams overlap upon composite dipole array 150.

Optionally, windows 128a, 128b, 129a and 129b can be provided to isolate the laser gain medium environment from the composite dipole array environment. For example, the gain medium may operate at sub-atmospheric pressure while the composite dipole array may operate at ambient pressure. The gases of the laser gain medium may also be different from those of the composite dipole array environment.

Furthermore, a transverse mode control assembly 140 can be provided to maintain operation of the laser oscillators in their $TEM_{oo}$ (fundamental) modes. One effective approach is to bring the laser beam into a focus and remove portions of the beam outside the Airy disk (in focal plane) with an aperture (spatial filtering).

Figure 2:
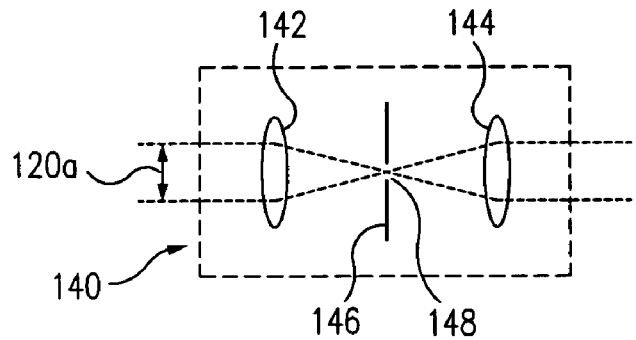
FIG. 2 shows a block diagram illustrating a transverse mode control using lenses according to one aspect of the present invention, wherein the transverse mode control is suitable for use in the THz radiation generator of FIG. 1.

FIG. 2 shows a transverse mode control that has been implemented using lenses. Laser beam 120 is brought to a focus 148 at aperture 146 by a lens 142 and is then subsequently collimated by a lens 144. In this manner, portions of the beam outside of the Airy disk defined by aperture 146 are removed thereby.

Figure 3:
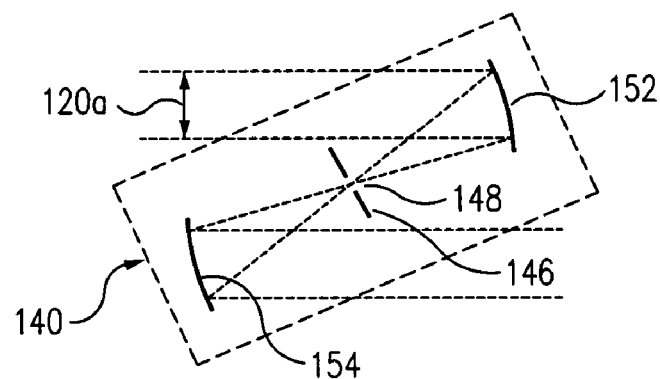
FIG. 3 shows a block diagram illustrating an alternative transverse mode control using mirrors according to one aspect of the present invention, wherein the transverse mode control is suitable for use in the THz radiation generator of FIG. 1.

FIG. 3 shows how the laser beam can alternatively be brought into focus with mirrors. Here, laser beam 120 is brought to a focus 148 by a mirror 152 and is then subsequently collimated by a mirror 154. As those skilled in the art will appreciate, such transverse mode control can thus be accomplished using any desired combination of lenses and mirrors.

Referring again to FIG. 1, each laser 120a and 120b can include means for reverse mode suppression, so that the beam inside the oscillator tends to propagate only in one direction, as indicated by arrows 134a and 134b. Such reverse mode suppression can be accomplished using well know principles. For example, lasers having built-in reverse mode suppression can be purchased off the shelf.

Lasers 120a and 120b can to include means for frequency selection. It is well known that gratings can be used to precisely select a lasing frequency in laser medium, such as the case of $CO_2$ lasers capable of supporting more than one laser transition. In lasers 120a and 120b laser frequency selection capability is provided, for example, by replacing the mirrors 126a and 126b with gratings that can be appropriately oriented so as to provide operation at desired frequencies.

Laser gain mediums 124a and 124b can comprise vibrationally and rotationally excited $CO_2$ gas that is known to exhibit laser gain at over seventy-five discrete wavelengths in the proximity of 10 micrometers. As discussed above, appropriate wavelength selection means can be provided to allow lasers 120a and 120b to operate only at particular predetermined wavelengths. Excitation means for the $CO_2$ gas can include DC electric discharge or microwave discharge. As those skilled in the art will appreciate, other excitation means can likewise be used with the present invention.

During operation, lasers 120a and 120b, generate traveling wave beams 132a and 132b, respectively. Beams 132a and 132b overlap upon composite dipole array 150 where, at resonance, a portion of the incident laser powers are converted into THz radiation 190 at frequency $f_1$-$f_2$ and this difference frequency propagates normal to the plane of composite dipole array 150. A portion of incident laser beams 132a and 132b that passes through composite dipole array 150 forms beams 133a and 133b, respectively. Beam 133a is reflected by mirrors 125a, 126a, and 127a back into gain medium 124a where it is amplified to reinforce beam 132a. Beam 132b undergoes a similar process in laser 120b, resulting in formation of beam 132b. In this manner, laser energy not converted into THz output in a single pass through the composite dipole array 150 is recovered and reused. Thus, conversion to THz radiation is a principal means for removal of laser energy from lasers 120a and 120b. Except for some losses due to diffraction and absorption, a significant part of the laser power generated by laser gain media 124a and 124b in lasers 120a and 120b is thus coupled into the composite dipole array 150, is converted into THz radiation, and emitted as a single frequency, continuous wave (cw) collimated THz beam.

According to one aspect of the present invention, composite dipole array 150 can be substantially larger in one or more transverse directions than the corresponding transverse dimensions of laser beams 132a and 132b inside their respective resonators. In this event, laser beams 132a and 132b can be expanded to a desired size using conventional beam expanders. Similarly, laser beams 132a and 132b can be compacted so as to accommodate use with a composite dipole array 150 having one or more smaller transverse dimensions. Thus, the cross-sections of laser beams 132a and 132b can generally be configured so as to match their sizes to the size and shape of composite dipole array 150.

Figure 4:
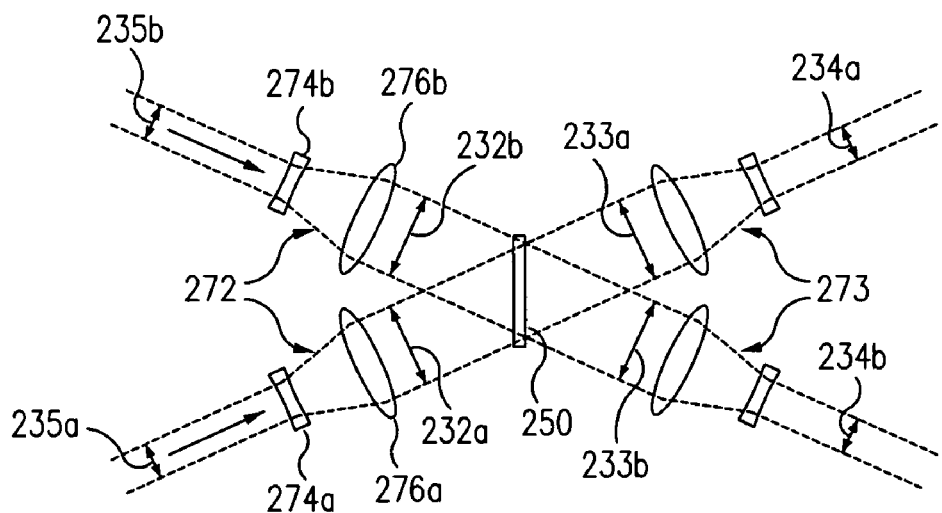
FIG. 4 shows a block diagram illustrating beam expanders according to one aspect of the present invention, wherein the beam expanders are suitable for use in the THz radiation generator of FIG. 1.

FIG. 4 shows one example of the use of beam expanders 272 to facilitate such modification of the laser beams 235a and 235b to correspond to the configuration of a composite dipole array 250. In this instance, composite dipole array 250 is substantially larger in at least one transverse dimension than the laser beams 235a and 235b. Gaussian type of beam expanders 272 formed by negative lenses 274a and 274b and positive lenses 276a and 276b expand the beams 235a and 235b to form expanded beams 232a and 232b that provide a more complete illumination of the composite dipole array 250.

Laser beams 233a and 233b, which are downstream with respect to the composite dipole array 250, are subsequently compacted to form beams 234a and 234b by compactors 273. Compactors 273 are essentially devices that are equivalent to expanders 272 operating in a reverse mode. Similar beam expanders can be used for the outputs of both lasers 120a and 120b of FIG. 1. The Gaussian type of beam expanders, consisting of at least a negative and a positive lens in each, maybe substituted by beam expanders with spatial filters incorporated in them, such as illustrated in FIG. 2. When beam expanders using transmissive optics are undesirable, the present invention can be practiced using beam expanders constructed from reflective optics (e.g., mirrors). See FIG. 3. Both transmissive and reflective beam expanders are well known in the art.

Figure 5:
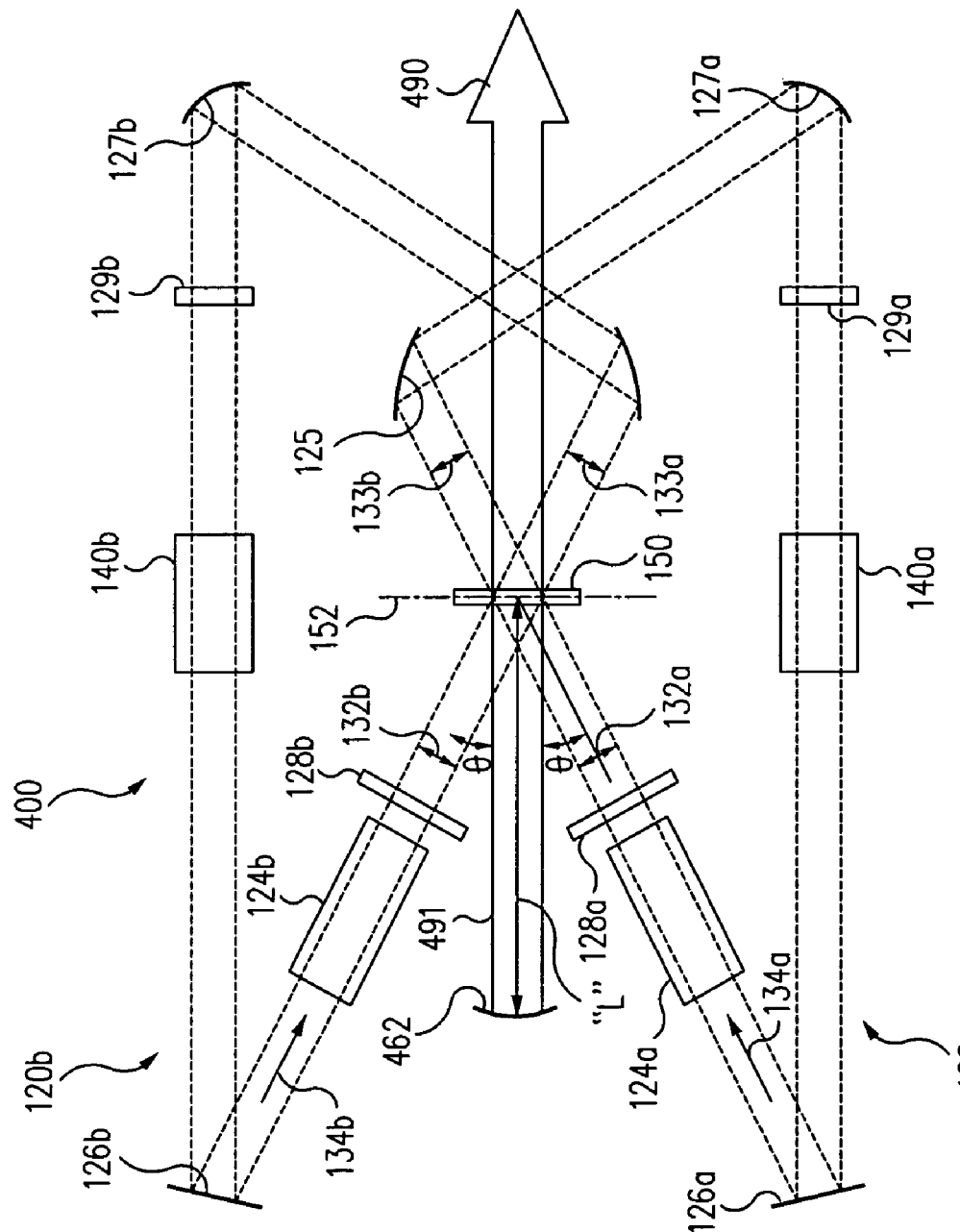
FIG. 5 shows a block diagram illustrating a THz radiation generator in accordance with another exemplary embodiment of the present invention.

FIG. 5 shows a THz generator 400 in accordance with another embodiment of the present invention. This embodiment is generally the same as the embodiment of FIG. 1, except that THz radiation 491 (which is transmitted to the left from composite dipole array 150 in FIG. 5) is redirected (reflected) by a mirror 462 to travel in the same direction (to the right in FIG. 5) as the THz radiation 490. Mirror 462 can be formed so that the shape of the reflected THz radiation 491 wavefronts matches the shape of the THz radiation 490 wavefronts. To assure that the reflected radiation 491 and radiation 490 add coherently, mirror 462 is placed a distance L from the dipole plane 152 of the composite dipole array 150 and L is chosen to be an integer number of one half of the THz radiation wavelength. Thus, the THz beams emitted in both direction from composite dipole array 152 interfere constructive to provide more power in the output beam and consequently to enhance the efficiency of one half of the THz electromagnetic radiation generation. Coherent addition of the electric field nearly doubles the E field (quadruples the power) in the outgoing THz beam.

Figure 6:
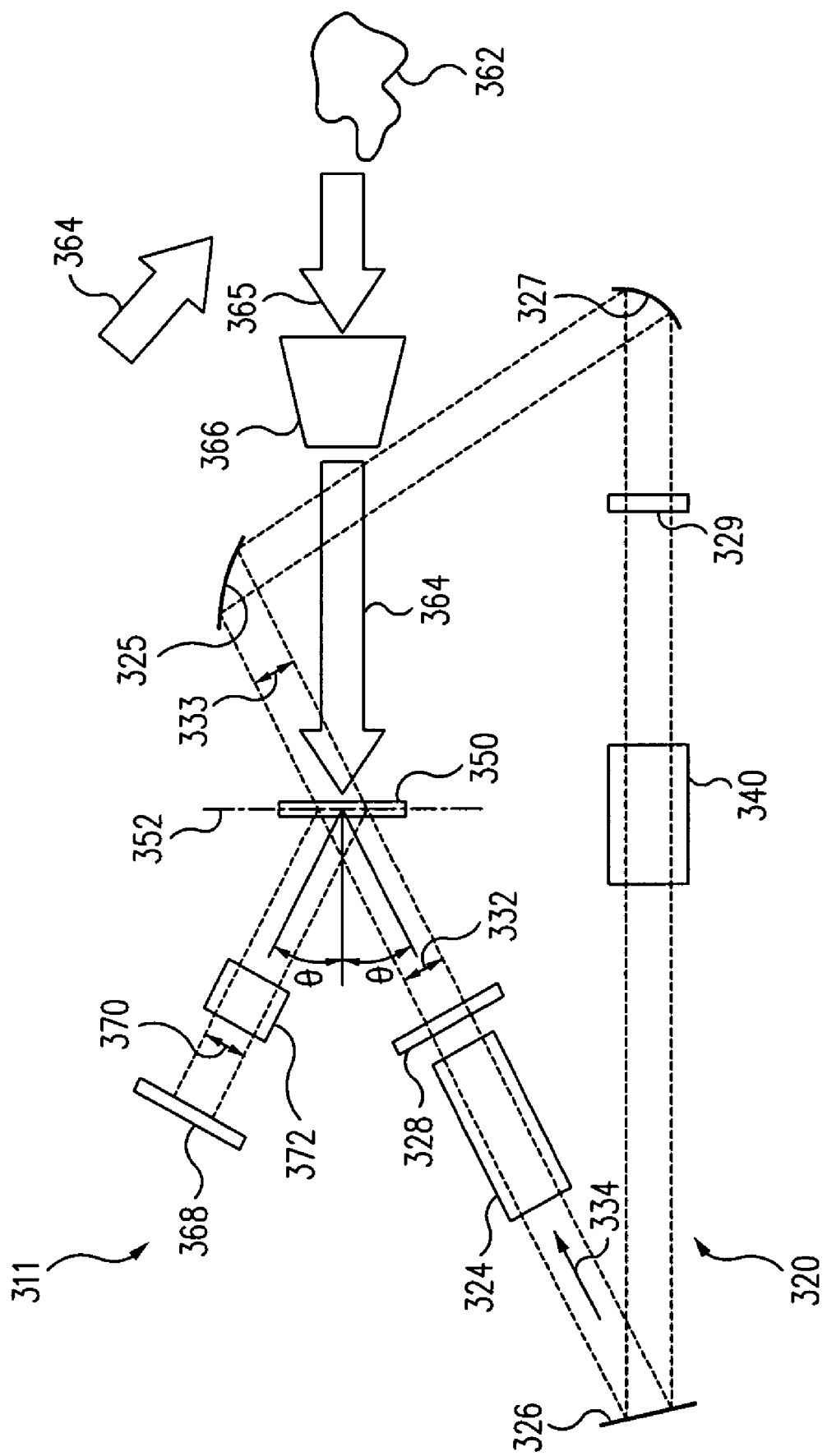
FIG. 6 shows a block diagram illustrating a THz imaging detector in accordance with another exemplary embodiment of the present invention.

FIG. 6 shows a THz imaging receiver 311 in accordance with another embodiment of the present invention. THz imaging receiver 311 comprises a laser 320, a composite dipole array 350, THz imaging optics 366, infrared (IR) imaging optics 372, and an infrared focal plane array 368. Laser 320 can be of the ring type (also known as traveling wave type) formed by a gain medium 324 and reflectors 325, 326, and 327. Reflector 326 can be either a flat mirror or a diffraction grating. Reflectors 325 and 327 can be curved (e.g., parabolic) mirrors.

Laser 320 generates a laser beam 332 that is incident upon composite dipole array 350 at an angle θ with respect to a normal of the plane of composite dipole array 350. Windows 328 and 329 can optionally be provided to isolate the laser gain medium environment from the composite dipole array environment. Furthermore, a transverse mode control assembly 340 can be provided to operate the laser 320 in its $TEM_{oo}$ mode.

Laser 320 can include appropriate means for reverse mode suppression, as discussed above, so that the beam inside the oscillator can propagate only in one direction as indicated by arrow 334. Laser 320 can include means for frequency selection, as discussed above. A laser gain medium 324 can comprise vibrationally and rotationally excited $CO_2$ gas that is known to exhibit laser gain at over seventy-five discrete wavelengths in the proximity of 10 micrometers. Appropriate wavelength selection means can be provided to allow laser 320 to operate only at a particular predetermined wavelength. Excitation means for the $CO_2$ gas can include electric discharge and microwave discharge. However, other excitation means can be used with the present invention.

During operation, laser 320 generates a traveling wave beam 332 that is incident upon composite dipole array 350 where, at resonance, a portion of the incident laser power is coupled into the micro-dipoles thereof. THz radiation 364 at frequency $f_5$ illuminating an object 362 is reflected from the object 362 as THz radiation 365 that enters THz imaging optics 366 and is formed thereby into a THz image of the object on composite dipole array 350. Composite dipole array 350 has an array of dipoles (micro-dipoles and macro-dipoles) of appropriate dimensions and arrangement for resonance at both laser frequency $f_4$ (for micro-dipoles) and at THz frequency $f_5$ (for macro-dipoles).

As a result of the interaction of THz radiation 364 with the collimated, single frequency laser beam 332 on the composite dipole array 350, infrared radiation 370 at respective frequencies $f_5-f_4$ and $f_5+f_4$ is generated and propagated at an angle θ with respect to a normal of the plane of composite dipole array 350. Infrared radiation 370 can be imaged onto a focal plane array 368 suitable for converting infrared radiation at these wavelengths into electric signals or visible and digitized images. In this fashion, the THz image of object 362 produced by THz imaging optics on composite dipole array 350 can be viewed at infrared wavelengths.

The portion of the incident laser beam 332 that passes through composite dipole array 350 defines beam 333. Beam 333 is reflected by reflectors 325, 326 and 327 into gain medium 324, where it is amplified so as to reinforce beam 332. In this manner, laser energy not coupled into the composite dipole array 350 in a single pass is recovered and reused. Except for losses due to diffraction and absorption, all of the laser power generated by the laser gain medium 324 in laser 320 is coupled to the composite dipole array 350 and is available for up-conversion of incident THz radiation of the THz image into infrared radiation.

Figure 7:
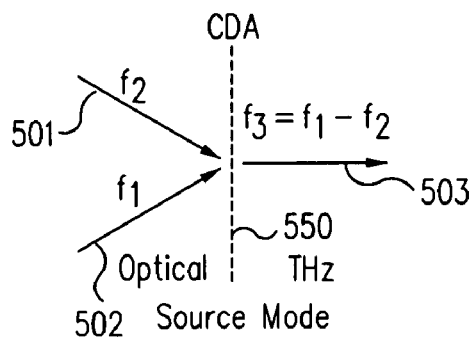
FIG. 7 shows a diagram illustrating the use of a composite dipole array (CDA) to convert optical electromagnetic radiation into THz electromagnetic radiation using the hybrid frequency conversion technique according to one aspect of the present invention.

FIG. 7 shows the frequency down-conversion from optical electromagnetic radiation in the IR part of the spectrum to THz electromagnetic radiation by irradiating a composite dipole array 550 with two coherent optical waves having respectively frequencies $f_1$ and $f_2$. The frequency difference $f_1-f_2$ is selected so as to provide the desired THz frequency $f_3$. Fortuitously, suitable sources with single frequency, stable outputs separated by frequencies in the THz domain are conveniently offered by $CO_2$ lasers, which have over seventy-five output lines in the vicinity of 10 μm. The large number of closely spaced lines offered by $CO_2$ lasers facilitates the selection of line pairs suitable for production of a choice of many thousands of different THz frequencies from 0.025 to over 5.0 THz. For example, mixing the 10.25 μm and 10.48 μm wavelengths yields an output with 639.5 GHz frequency in the middle of an atmospheric window with low atmospheric absorption.

Figure 8:
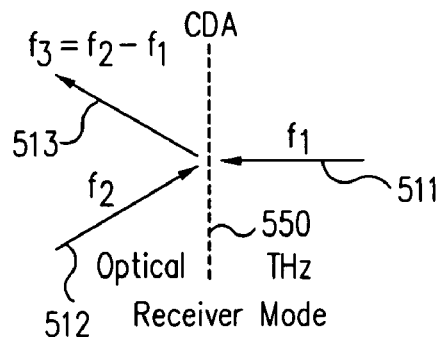
FIG. 8 shows a diagram illustrating the use of a composite dipole array to covert THz electromagnetic radiation into optical electromagnetic radiation using the hybrid frequency conversion technique according to one aspect of the present invention.
Figure 9:
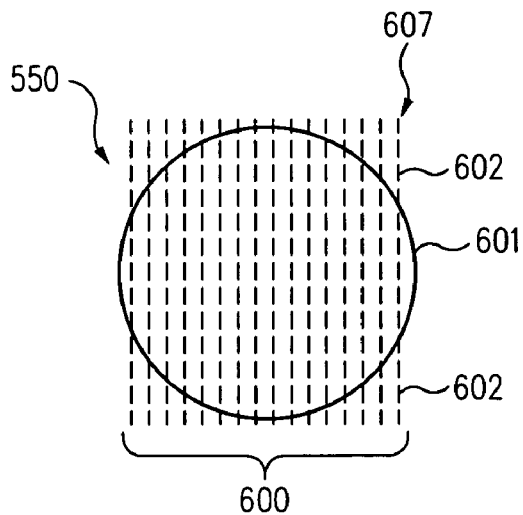
FIG. 9 shows a diagram illustrating a planar composite dipole array according to one aspect of the present invention.

FIG. 8 shows a frequency up-conversion from THz into the optical IR regime where a THz image signal $f_1$ is imaged onto a composite dipole array 550 where it is mixed with an external single frequency optical field having frequency $f_2$ to generate optical signals at frequencies $f_3$ and $f_4$ representing the THz image that can be viewed with focal plane arrays (FPAs) of conventional infrared cameras. It is worth while to note that $f_3=f_2-f_1$ and $f_4=f_2+f_1$.

In principle, the same general layout of composite dipole array can be used for both down-conversion and up-conversion, although in practice different materials may be used. The HFC technique can be used in either continuous wave (cw) or pulsed mode. An advantage of the pulsed mode is the possibility to improve the signal-to-noise ratio (SNR).

FIGS. 9-12 show that composite dipole array 550 can be defined by an array of one-dimensional dipole arrays that define macro-dipoles 607, which are in turn defined by arrays of substantially identical individual micro-dipoles 602. Micro-dipoles 602 are resonant at a predetermined higher frequency and arranged in a one-dimensional (tip-to-tip) configuration, so as to define larger macro-dipoles 607 that are resonant at a predetermined lower frequency. A plurality of such linear macro-dipoles 607 placed side-by-side define a planar, two-dimensional composite dipole array (CDA) 550.

An interference zone 601 is defined by that area of composite dipole array 550 where two laser beams are incident thereon so as to produce interference that provides the difference frequency that is subsequently re-radiated by composite dipole array 550 as THz electromagnetic radiation (503 of FIG. 7) during the down conversion process of source mode operation according to one aspect of the present invention. This is also the interference zone where THz electromagnetic radiation (511 of FIG. 8) interferes with optical radiation (512 of FIG. 8) so as to produce the difference frequency (513 of FIG. 8) that is subsequently re-radiated by composite dipole array 550 as optical radiation during the up conversion process of receiver mode operation according to one aspect present invention.

Figure 10:
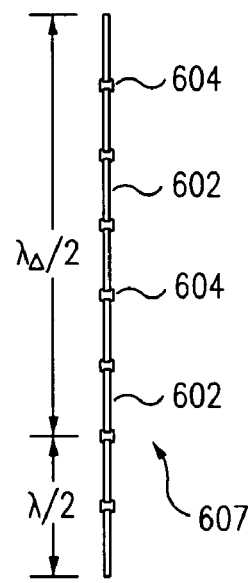
FIG. 10 shows a block diagram illustrating a single linear dipole array of the antenna of FIG. 9, more clearly showing one of the individual non-linear resonant circuits and micro-dipoles thereof.
Figure 11:
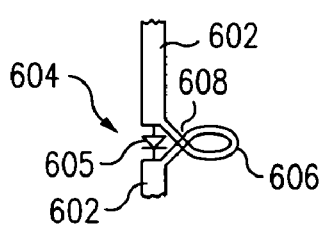
FIG. 11 shows a block diagram illustrating the diode, capacitor, and inductor that schematically illustrates each of the non-linear resonant circuits formed intermediate adjacent micro-dipoles of the linear dipole array of FIG. 10.

As shown in FIG. 10, adjacent micro-dipoles 602 are interconnected by non-linear resonant circuits (NLRCs) 604. As shown in FIG. 11, the non-linear resonant circuits 604 comprise a diode 605 or some other non-linear component. The non-linear resonant circuits also comprise at least one capacitor 608 and one inductor 606. These circuit components may be either lumped elements as shown in FIG. 11 or distributed.

For operation in the optical and THz regimes, if the circuit components are lumped elements, their mechanical dimensions are very small. For example, dimensions of capacitors is just a fraction of a micron, the line width of the micro-dipole conductors would be approximately 300 nm or less.

Figure 12:
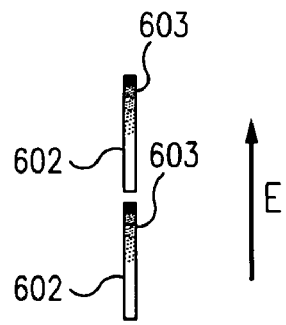
FIG. 12 shows a diagram illustrating a "snap-shot" of electrons moving toward the upper ends of individual micro-dipoles, such as occurs, if the individual micro-dipoles are not connected to one another.

FIG. 12 shown electrons in individual micro-dipoles 602 accumulating at one end (the upper end) thereof in response to the application of a sinusoidally varying electric field (such as that of optical electromagnetic radiation incident upon composite dipole array 550) when the micro-dipoles are unconnected. Current merely flows to one end of each micro-dipole, instead of flowing from micro-dipole to micro-dipole when the micro-dipoles are interconnected tip to tip to facilitate resonance and re-radiation at the macro-dipole frequency. Thus, the use of non-linear resonant circuits 604 allows a one-dimensional string of micro-dipoles 602 to function as a single macro-dipole 607 by facilitating current flow between micro-dipoles 602 at the difference frequency only.

Suitable techniques for fabricating composite dipole array 550 include e-beam lithography. Note that although the physical footprint of composite dipole array 550 is rather small, at resonance it nevertheless intercepts a large portion of incident radiation thereby enabling high conversion efficiencies.

Figure 13:
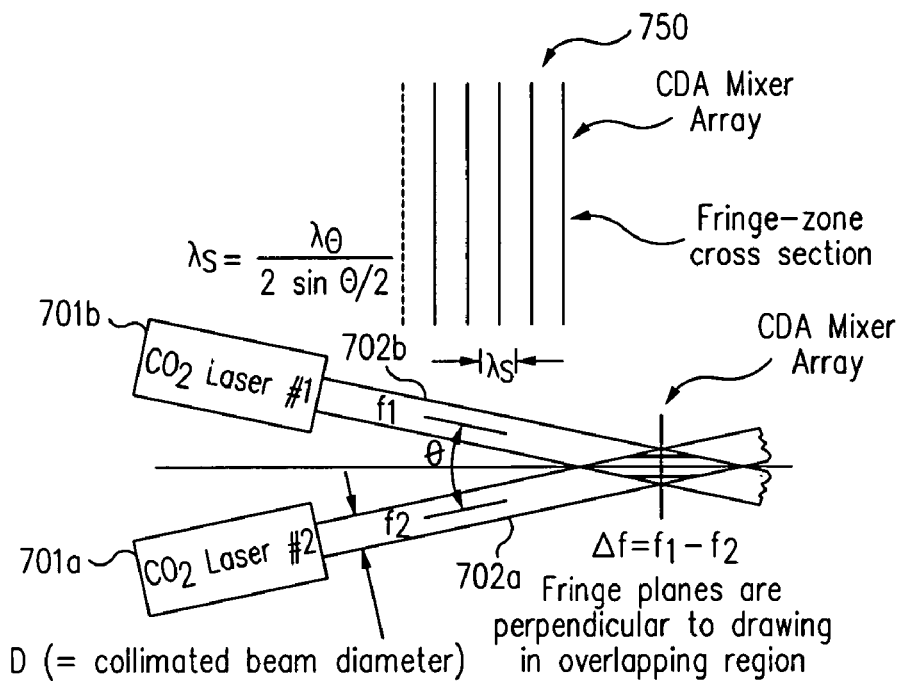
FIG. 13 shows a diagram illustrating the use two $CO_2$ lasers configured to radiate at two different frequencies and oriented at angular positions with respect to one another, wherein the two $CO_2$ lasers are configured to irradiate a planar composite dipole array so as to generate THz electromagnetic radiation according to one aspect of the present invention.

FIG. 13 shows the HFC method for THz electromagnetic radiation generation. Two $CO_2$ lasers 701a and 701b provide laser beams 702a and 702b at predetermined closely spaced frequencies and at angular positions with respect to one another so as to irradiate a resonant planar composite dipole array 750, thereby generating a THz electromagnetic radiation output propagating at normal incidence away from the composite dipole array 750.

Figure 14:
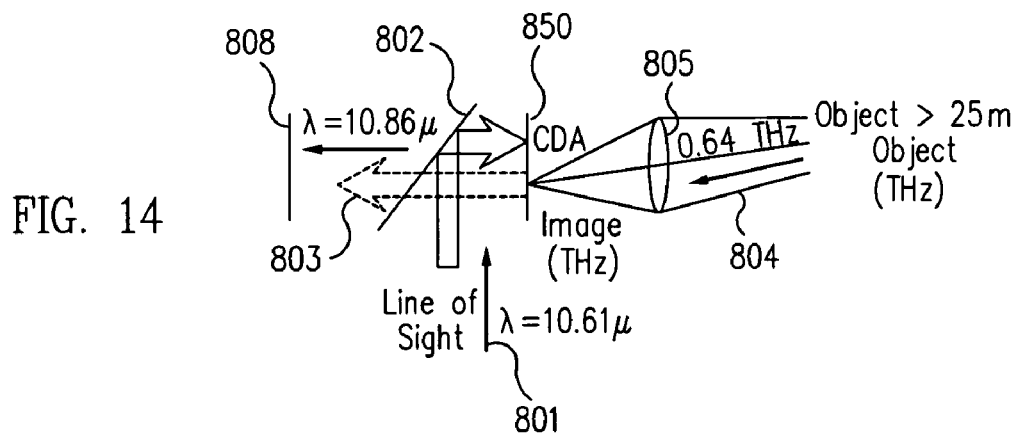
FIG. 14 shows a block illustrating the use of a composite dipole array to perform frequency up-conversion, wherein a THz electromagnetic signal is mixed with a $CO_2$ laser beam to provide an infrared output suitable for imaging, according to one aspect of the present invention.

FIG. 14 shows the method for using a composite dipole array 850 as a THz electromagnetic radiation imaging receiver. The composite dipole array may be a 200×200 pixel array where each pixel consists of a one-dimensional (macro) dipole array, for example. This concept is analogous to the use of composite two-dimensional dipole array 750 as a THz electromagnetic radiation source, as shown in FIG. 13 and discussed above. The frequency up-conversion occurs on composite dipole array 850, where an imaged THz signal 804 is mixed with a selected $CO_2$ laser line 801.

An image field 803 radiated by composite dipole array 850 contains two frequency components. One frequency component is at a frequency that is the sum of the THz frequency and the $CO_2$ laser frequency. The other frequency component is at a frequency that is the difference between the THz frequency and the $CO_2$ laser frequency. The two frequencies can be separated spectrally or can both be used together to enhance the signal to noise ratio.

The THz image thus upshifted to infrared frequencies can also be received on a conventional focal plane array, viewed by an infrared imager, digitized, recorded and displayed in various formats. A dichroic mirror 802 can be used to direct infrared electromagnetic radiation to composite dipole array 805 and to allow infrared radiation from composite dipole array 805 to pass therethrough to an image sensor array 808.

Field emission devices (FEDs) are micro-vacuum tubes and have gained recent popularity as alternatives to conventional semiconductor devices. Typical advantages associated with FEDs include much faster switching, temperature and radiation insensitivity, and easy construction. Applications include the construction of discrete active devices, high density static random access memories, displays, radiation hardened military equipment, and temperature insensitive devices for use in space.

Recently, lateral FEDs have emerged as an alternative to traditional vertical emitter devices. Lateral FEDs have many advantages in high-speed and high frequency applications because of their simple fabrication, precise control of electrode distances, and low capacitances.

The sharp radius of curvature (which can be less than 100 Å) around the edge of the thin-film cathode (emitter) in an FED produces the high intensity electric field necessary to cause the emission of electrons. This phenomenon is known as field emission. Unlike in traditional vacuum tubes with hot cathodes, or Schottky devices with warm cathodes, FEDs operate with the cathode at ambient temperature and thus have cold cathodes.

Figure 15:
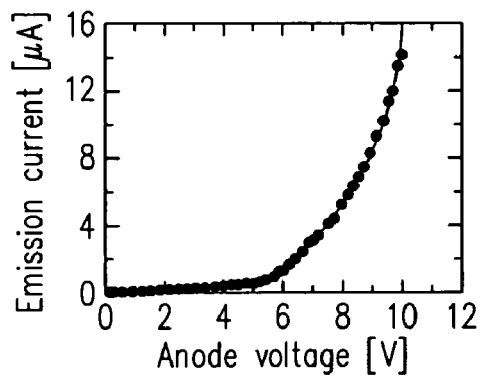
FIG. 15 shows a chart illustrating the I-V (emission current vs. anode voltage) characteristics of an exemplary field emission (FED) diode device.

In an FED, the emitter tip of the cathode is typically separated from an anode by a distance of less than 1 micron. Due to the extreme closeness of the emitter to the anode, operating voltages in FED are much lower than in traditional vacuum tubes. FIG. 15 shows that turn-on voltages as low as few Volt/μm and emission currents up to milliamps per tip are attainable.

Figure 16:
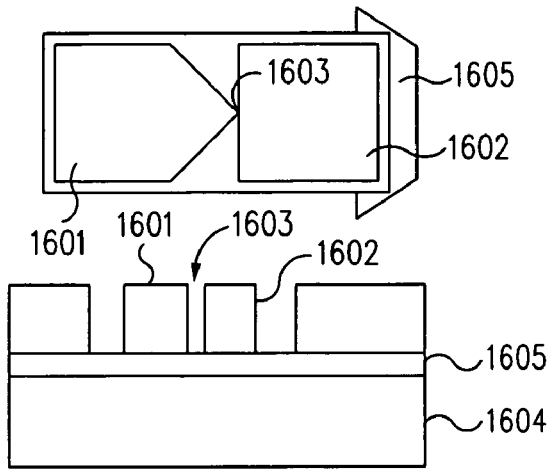
FIG. 16 shows a diagram illustrating a micro-miniature FED configured as a diode according to one aspect of the present invention.
Figure 17:
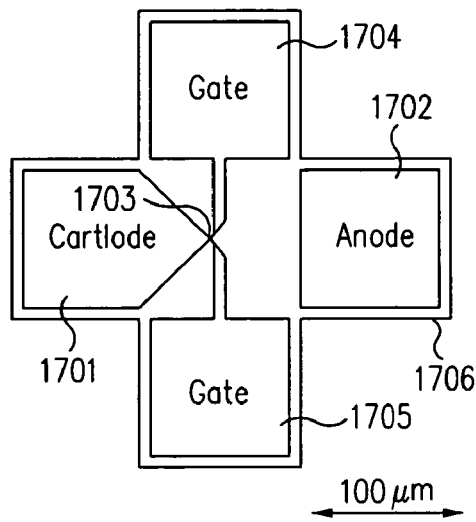
FIG. 17 shows a diagram illustrating a micro-miniature FED configured as a triode according to one aspect of the present invention.

FIGS. 16 and 17 shown micro-miniature FEDs configured as diodes and triodes. With particular reference to FIG. 16, the diode FED comprises a silicon cathode 1601 and a silicon anode 1602 formed upon a silicon substrate 1604. A gap 1603 is formed between the tip of the cathode 1601 and the anode 1602. An oxide layer 1605 electrically insulates the cathode 1601 and the anode 1602 from the substrate 1604.

With particular reference to FIG. 17, the triode FED comprises a silicon cathode 1701 and a silicon anode 1702 similarly formed upon a silicon substrate. A gap 1703 is formed between the tip of the cathode 1701 and the anode 1702. First 1704 and second 1705 gate members define a gate within the gap 1703. An oxide layer 1706 electrically insulates the cathode 1701, the gate electrodes, 1704 and 1705 and the anode 1702 from the substrate.

Suitable materials for the emitters include most metals (especially refractory metals), silicon, and nitrogen-doped diamond. To reduce device turn-on voltage, the cathode-anode separation should be minimized, the cathode tip radius should be made as small as practically possible while maintaining reproductability, and the cathode material is chosen to have a low work function. Using UV lithography cathode-anode separations down to about 300 nm have been achieved. Using electron beam lithography cathode-anode separations down to less than 30 nm have been achieved. Such small dimensions facilitate the use of turn-on voltages in the range of 100 mV.

Micro-machined lateral FEDs combine the advantages of electron transport in vacuum with the ease of solid-state microfabrication techniques. As a result, lateral FEDs offer the distinct advantages of high specific power and efficiency, compactness, and ease of thermal management. In radio frequency devices FEDs provide higher transconductance, reduced ionization and breakdown, lower power dissipation and heating, and low capacitance.

The non-linear resonant circuit is a critical part of a composite dipole array because it enables the efficient generation of the difference (THz) frequency. In particular under ideal conditions, the non-linear resonant circuit provides open circuits at the high ($CO_2$ laser) frequencies ($\lambda \sim 10$ μm) and short circuits at the (low) difference (THz) frequency ($\lambda > 50$ μm). Thus, at high frequencies adjacent dipoles in the linear array are isolated from each other and resonate as individual unconnected half-wave dipoles. On the other hand, at the THz frequencies the non-linear resonant circuit becomes short circuits, thereby connecting adjacent dipoles into the longer half wave dipole resonating at the difference (THz) frequency. The capacitance of conventional high frequency semiconductor diodes is too large to allow efficient operation in the THz frequency range of interest (e.g., approximately 30 THz).

Various metal-oxide-metal (MOM) diodes have been used during the past decade that worked satisfactorily (Ni—NiO—Ni diodes, for example). However these structures need a bias voltage for proper function. While the means for bias can be incorporated into the composite dipole array, it substantially complicates the design and fabrication of the array elements. Schottky diodes used in high frequency (mm wave) receivers are the standard technology for operation at room temperature. Recent advances in this technology include III-V semiconductor on quartz substrates that have shown much reduced parasitic capacitances. Planar diode mixers of this type have been operated with noise performance at frequencies above 3 THz. GaAs Schottky diodes have been used as antennas coupled square law detectors. Whiskered diode triplers have operated at frequencies above 1 THz. Semiconductor diodes introduce significant parasitic capacitance and noise into the nonlinear resonant circuits. In addition, fabrication of composite dipole arrays with high frequency, zero bias semiconductor diodes would require multiple fabrication steps involving molecular beam epitaxy (MBE) and electron beam lithography. This increases fabrication risks and reduces manufacturing yield. As a result, development of such a fabrication process would be very costly and risky.

Figure 18:
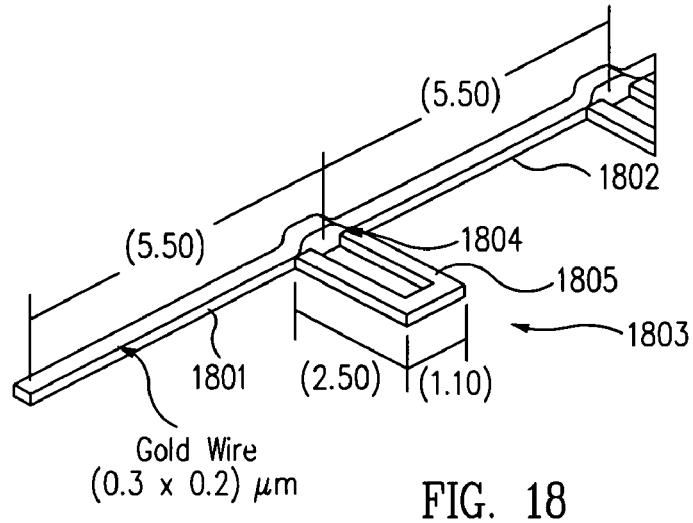
FIG. 18 shows a diagram illustrating two adjacent dipoles connected by a non-linear resonant circuit according to one aspect of the present invention.
Figure 19:
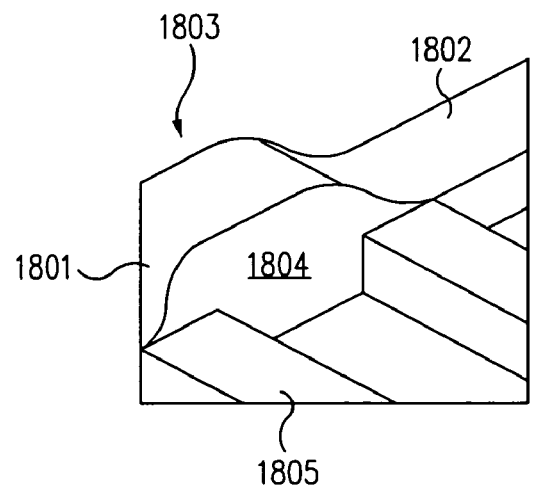
FIG. 19 shows a diagram illustrating an enlarged view of the intersection of the two adjacent dipoles of FIG. 18, according to one aspect of the present invention.

FIGS. 18 and 19 show a design for electrically interconnecting two adjacent dipoles 1801 and 1802 via a non-linear resonant circuit 1803 using a planar-type semiconductor diode 1804 with its capacitance and a shortened short circuited transmission-line (less than $\lambda/4$ in length) as an inductor 1805. Dipoles 1801 and 1802 can comprise gold wire having cross-sectional dimensions of 0.3×0.2 μm or less. Diode 1804 can comprise of a backward tunnel diode (BTD) for example.

By way of contrast, the present invention discloses a composite dipole array fabricated using field emission diodes (FEDs) that have a good frequency response in the THz regime, have very low parasitic capacitance, have a predictable performance, are very simple, and can be produced reliably in a single step as a part of the composite dipole array fabrication by e-beam lithography. FED diodes are readily integrated into the composite dipole array micro-dipole structures using established technologies including optical lithography, UV lithography, E-beam lithography, and x-ray lithography.

Figure 20:
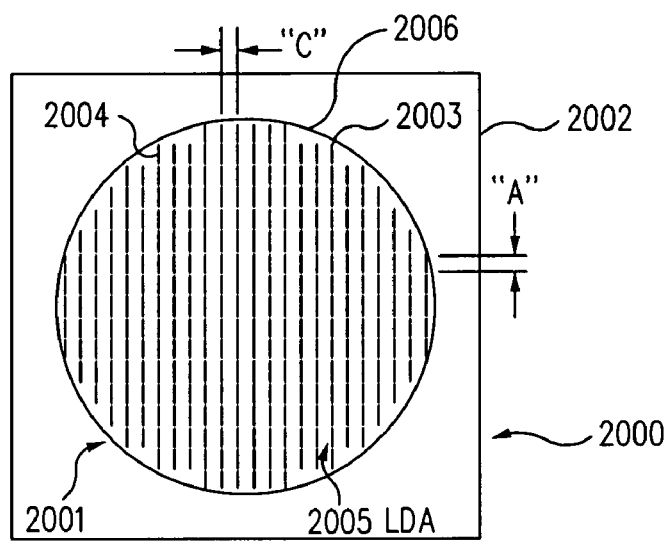
FIG. 20 shows a diagram illustrating a composite dipole array in accordance with an aspect of the present invention.

FIG. 20 shows a composite dipole array 2000 in accordance with an embodiment of the present invention. Composite dipole array 2000 comprises a substrate 2002 and a plurality of one-dimensional dipole arrays (LDAs) 2005 formed upon substrate 2002. Elements of the macro-dipole array 2005 can be arranged in in-line configurations or rows 2003. Columns of the macro dipoles 2005 can be generally parallel with respect to each other and will be formed so as to have a constant lateral spacing, dimension C, with respect to one another. The numbers of macro dipole strings 31 can be chosen to fit within a perimeter 2006 which is typically circular or slightly elliptical and size of this perimeter is determined by the two incident, superimposed laser beam. However, the grouping and lengths of the macro dipole strings 2005 can be configured according to any other desired perimeter shape including, square, rectangular, triangular, polygonal, or even an irregular shape. All macro dipoles 2004 in a composite dipole array 2000 would be identical, and have the same length, dimension A. The spacing between adjacent macro-dipole strings, dimension C, can be $(2n+1)\lambda_L/2$, where $n=0,1,2, \ldots$ is an integer and $\lambda_L$ is the wavelength of the difference frequency $f_3$ of the derived THz radiation modified by the presence of substrate reactive index and other factor.

Figure 21:
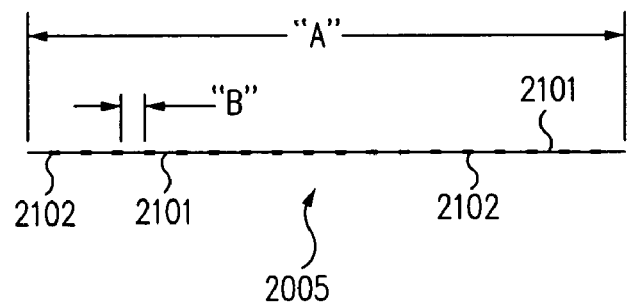
FIG. 21 shows a block diagram illustrating a single one-dimensional dipole array of FIG. 20.

FIG. 21 shows that each macro-dipole consists of a string of micro-dipoles 2005. Adjacent micro-dipoles 2101 are electrically interconnected to each other by a non-linear resonant circuit (NLRC) 2102. All micro-dipoles 2101 in each macro dipole array element 2005 are of the same length, dimension B, which is chosen to correspond approximately to the half-a-wavelength of electromagnetic radiation of the incident laser beams, modified by the refractive index of the substrate. Each macro dipole 2005 contains an integral number of micro-dipoles 2101, wherein the integral number is chosen so that the overall electrical length, related to dimension A, of the macro-dipole 2005 corresponds to half-a-wavelength of electro-magnetic radiation at the difference frequency $f_3$. The macro dipole arrays 2005 constructed in this manner are resonant at both frequency $f_H(f_1+f_2)$ and frequency $f_L(f_3=f_1-f_2)$. That is, individual micro-dipoles resonant at the higher frequency $f_H$, while the macro dipole 2005 are resonant at the lower frequency $f_L$. This condition may be referred to as dual-resonance.

EXAMPLE 1

For simplicity, the following example ignores the presence of any dielectric materials, such as a dipole array support substrate, and also assumes that the resonant dipole's conductivity contains no imaginary part. A macro dipole 2005 intended to resonate at $f_H=28.595$ THz (the frequency of a $CO_2$ laser operating at the 10.49 micrometer wavelength) should comprise micro-dipoles 2101 having a length, dimension B, of approximately 7.2 micrometers, which includes 5.2 micrometers of physical dipole length and 2 micrometers of separation distance. If additionally, the macro dipole 2005 is intended to resonate at $f_L=0.640$ THz, then the macro dipole length, dimension A, should be approximately 234 micrometers, which corresponds to 32 in-line micro-dipoles 2101.

Substrate 2002 can be formed of dielectric material exhibiting very low electrical conductivity at the frequencies $f_L$ and $f_H$. In at least some embodiments of the invention, substrate 2002 can be thin (from about 0.1 micrometer to about 1 millimeter) and exhibits low absorption of electromagnetic radiation at the frequencies $f_L$ and/or $f_H$. Examples of suitable materials for the substrate 2002 include glass, fused silica, sapphire, silicon, gallium arsenide, germanium, polycrystalline diamond, diamond-like films, single crystal diamond, zinc selenide, cadmium selenide, and cadmium telluride.

Micro-dipoles 2001 can be formed of materials exhibiting good electrical conductivity at the frequencies of $f_L$ and $f_H$. Examples of materials for micro-dipoles 2101 include copper, gold, silver, tungsten, molybdenum, and refractory metals. As those skilled in the art will appreciate, the selection of materials for the substrate and the dipoles depends on the choice of frequencies $f_H$ and $f_L$.

Figure 22:
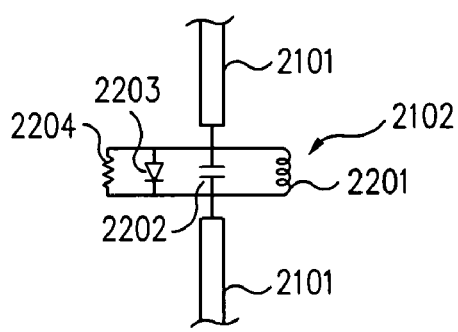
FIG. 22 shows a schematic diagram illustrating one of the non-linear resonant circuits of the one-dimensional dipole array of FIG. 21.

FIG. 22 shows a schematic of an exemplary non-linear resonant circuit 2102. Non-linear resonant circuit 2102 comprises at least a diode 2203 a capacitor 2202 and inductor 2201. Losses in the nonlinear resonant circuit would be represented by an ohmic component 2204. Parameters of the components of the non-linear resonant circuit 2102 are chosen so that non-linear resonant circuit 2102 provides higher impedance (e.g., substantially an open circuit) to the flow of electrical current at frequency $f_H$ and provides lower impedance (e.g., substantially a short circuit) to flow of electrical current at frequency $f_L$.

Figure 23:
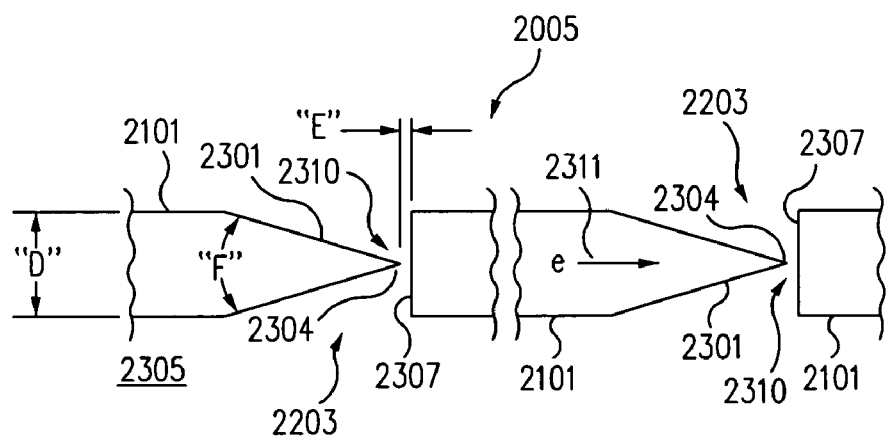
FIG. 23 shows a diagram illustrating further detail of the physical construction of one of the various versions of the nonlinear element of the one-dimensional dipole array of FIG. 21.
Figure 24:
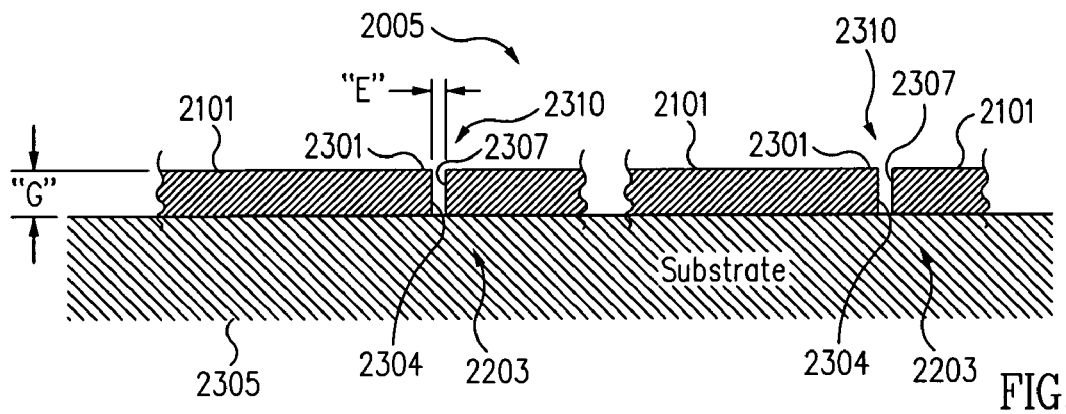
FIG. 24 shows a cross-sectional view illustrating further detail of the physical construction of one of the various versions of the nonlinear element of the one-dimensional dipole array of FIG. 21.

FIGS. 23 and 24 show a plan view and a cross-sectional view, respectively, of an exemplary linear dipole array 2005. A macro-dipole 2005 comprises micro-dipoles 2101 that are electrically connected by diodes 2203. Each diode 2203 further comprises a cathode 2301 and anode surface 2307 separated by a gap 2310 having dimension E. The cathode 2301 has an apex portion with angle F terminated by an emitter tip 2304. Dimension E of gap 2310 can be made sufficiently small so that significant electron current is emitted from the cathode 2301 onto the anode surface 2307 at a relatively low electrical potential across gap 2310. It has been established that a device constructed in this fashion preferentially supports electron flow in the direction indicated by arrow 2311, and thus functions as a diode.

Dimension E of gap 2310 can be formed to be less than 1 micrometer and can be as small as a few nanometers. In practice, the lower bound on dimension E is limited by the availability of suitable manufacturing processes. The width, dimension D, of the micro-dipoles 2101 is preferably less than 10% of the micro-dipole length, dimension B. FIG. 24 is a cross-sectional view of linear dipole array 2005 showing the thickness, dimension G, of the micro-dipoles 2101. The thickness, dimension G, is usually less than the micro-dipole width, dimension D.

EXAMPLE 2

Using the macro-dipole and micro-dipole dimensions from Example 1, an example of a suitable choice for the micro-dipole width, dimension D, is approximately 200 nanometers and an example of a suitable choice for the micro-dipole thickness, dimension G, is approximately 100-150 nanometers.

Figure 25:
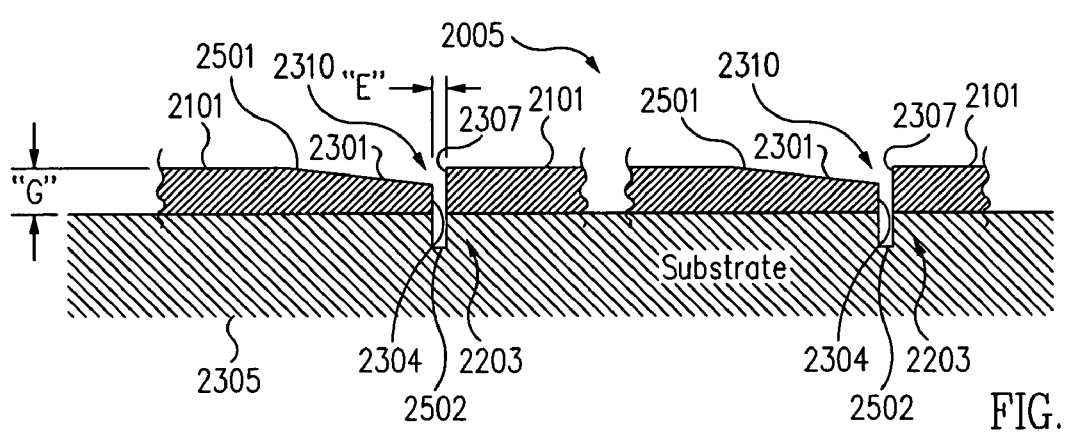
FIG. 25 shows a cross-sectional view illustrating an alternative configuration of the linear dipole array of FIG. 21, wherein trenches are formed in the substrate to mitigate undesirable perturbation of the electric field in the gap.

FIG. 25 shows a cross-sectional view of linear dipole array 2005 where the substrate 2305 has trenches 2502 formed therein is shown. Trenches 2502 are intended to reduce undesirable perturbation to the electric field in gap 2310 caused by substrate 2305. The width of the trenches 2502 is preferably the same or greater than the width, dimension E, of gap 2310 and the depth of the trenches 2502 is preferably about the same as the thickness, dimension G, of micro-dipoles 2101 or deeper. Cathode 2301 can optionally have a slope 2501, such that the thickness thereof gradually decreases as the cathode 2301 approaches the gap 2310.

Figure 26:
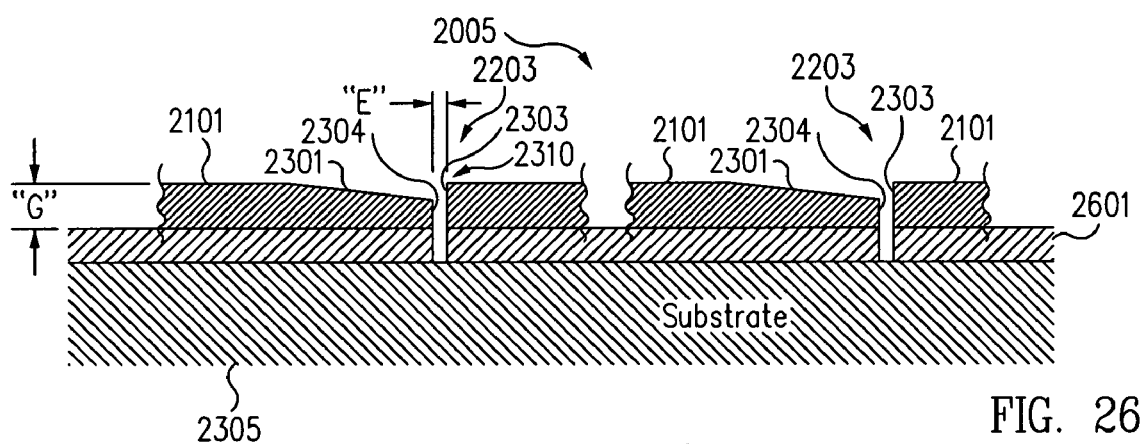
FIG. 26 shows a cross-sectional view illustrating an alternative configuration of the linear dipole array of FIG. 21, wherein an insulating layer is formed between the micro-dipoles and the substrate.

FIG. 26 shows a cross-sectional view of part of a macro dipole 2005 where an insulating layer 2601 is formed between micro-dipoles 2101 and substrate 2305. Insulating layer 2601 can be constructed as one or more dielectric layers. In one embodiment of the present invention, the dielectric layers can be constructed so that insulating layer 2610 is highly reflective at the frequency $f_H$ and/or frequency $f_L$. In another embodiment of the present invention, the dielectric layers can be constructed so that insulating layer 2610 is highly transmissive at the frequency $f_H$ and/or frequency $f_L$. For example, an insulating layer with quarter wave thickness in the dielectric layer will result in cancellation of the Fresnel reflections off of its boundaries.

Figure 27:
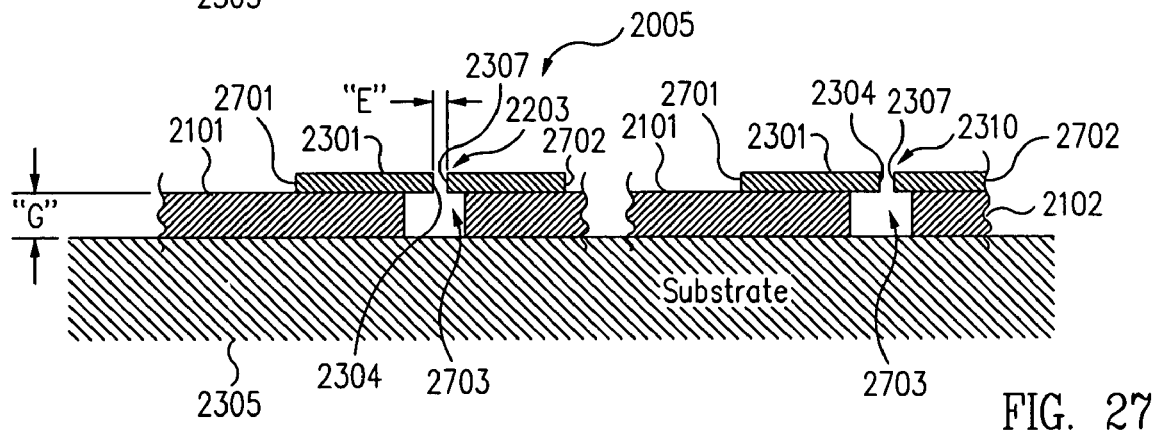
FIG. 27 shows a cross-sectional view illustrating an alternative configuration of the linear dipole array of FIG. 21, wherein the anodes and cathodes of the micro-dipoles are formed of different materials with respect to the remainder of the micro-dipoles.

FIG. 27 shows a cross-sectional view of part of an alternate macro dipole 2005, wherein 25 the diode 2203 is formed by a cathode layer 2701 and an anode layer 2702 that cooperate to define a gap 2703 therebetween. This embodiment of the macro dipole allows anode 2307 and cathode 2301 to be constructed from different materials with respect to the micro-dipoles 2101. For example, micro-dipoles 2101 can be constructed from gold, which has good electrical conductivity but can sustain only a limited current density without damage, whereas the anode layer 2702 and cathode layer 2701 can be constructed from refractory metal that has a higher damage threshold. In addition, the cathode layer material can be impregnated or coated with suitable materials having a low work function, such as ZrO or BaO. Other preferred materials for construction of anode layer 2702 and cathode layer 2701 include doped diamond.

Figure 28:
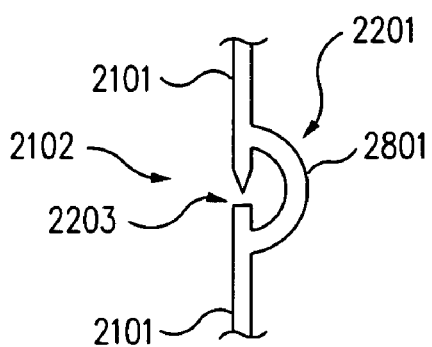
FIG. 28 shows a diagram illustrating an exemplary embodiment of the non-linear resonant circuit of FIG. 22, wherein an inductor is formed by an arc-shaped conductive path between adjacent micro-dipoles.
Figure 29:
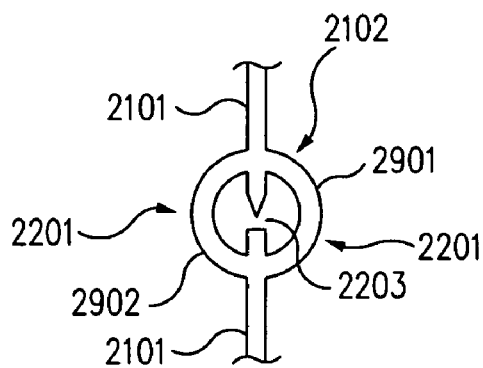
FIG. 29 shows a diagram illustrating an exemplary embodiment of the non-linear resonant circuit of FIG. 22, wherein the inductor is formed by two arc-shaped conductive paths between adjacent micro-dipoles.
Figure 30:
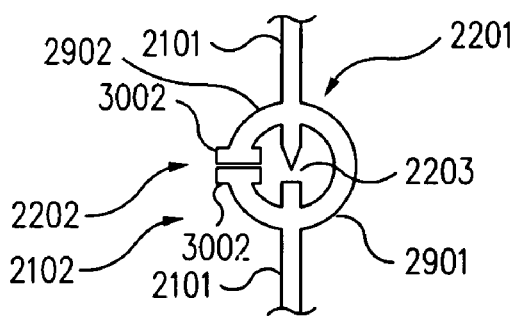
FIG. 30 shows a diagram illustrating an exemplary embodiment of the non-linear resonant circuit similar to that of FIG. 29, wherein a capacitor has been added to one of the arc-shape conductive paths.
Figure 31:
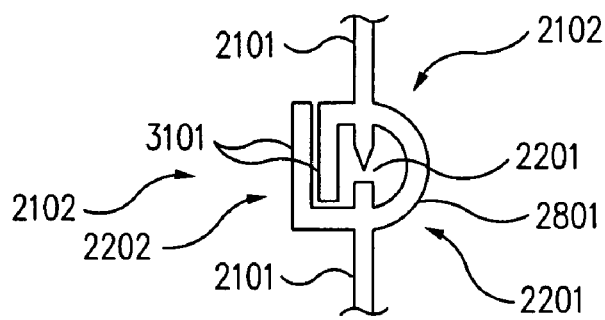
FIG. 31 shows a diagram illustrating an exemplary embodiment of the non-linear resonant circuit similar to that of FIG. 30, wherein the capacitor has a different shape.

FIGS. 28-32 show different embodiments of non-linear resonant circuit 2102. FIG. 28 shows a non-linear resonant circuit 2102 comprising a diode 2203 its capacitance and an inductor 2201, wherein inductor 2201 is created by an arc-shaped conductive path 2801 between adjacent micro-dipoles 2101. FIG. 29 shows non-linear resonant circuit 2102 having two parallel inductors 2201 defined by two arc-shaped conductive paths 2901 and 2902. FIG. 30 shows non-linear resonant circuit 2102 having a capacitor 2202 formed in one of the two arch-shaped conductive paths 2902. Capacitor 2202 comprises plates 3002. Optionally, capacitors could be similarly formed in both of the arch-shaped conductive paths 2901 and 2902. FIG. 31 shows non-linear resonant circuit 2102 similar to that of FIG. 30, but having a capacitor 2202 with a different shape. Capacitor 2202 comprises plates 3101.

Figure 32:
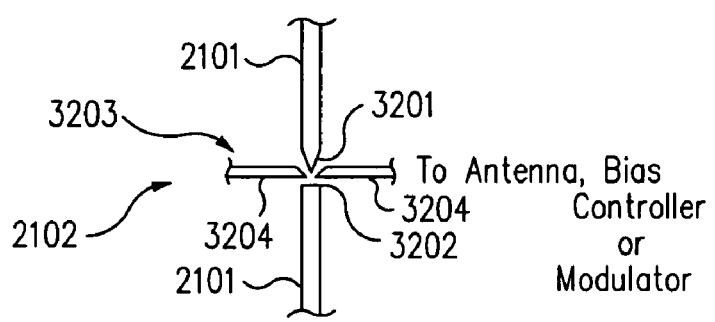
FIG. 32 shows a diagram illustrating an exemplary embodiment of the non-linear resonant circuit of FIG. 22, wherein the non-linear resonant circuit comprises a triode.

FIG. 32 shows a non-linear resonant circuit 2102 comprising a triode that includes a cathode 3201, an anode 3202 and a grid 3203 defined by two electrodes 3204. Using such a triode allows independent control of the electric field between cathode 3201 and anode 3202 and thus provides control over the current that flows therebetween. Such current control can be used to either provide a static bias that increases the threshold voltage or it can be applied dynamically to modulate a composite dipole array's resonance conditions, such as the Q of resonant circuit. Electric signals can be applied to grid 3203 either via wired connections to outside sources, or by connecting the grid 3203 to suitable electromagnetic radiation antennas. In this fashion the output electromagnetic radiation of the composite dipole array can be modulated. Such modulation may be suitable, for example, for communication purposes.

The composite dipole array of the present invention may optionally include means for tuning and/or modulation of composite dipole array resonant frequencies by superimposed magnetic and/or electric fields. Such modulation is suitable for generation of amplitude-modulated (AM) and frequency-modulated (FM) electromagnetic radiation. In particular, superimposed magnetic fields affect the mobility of electrons in the dipoles and the non-linear resonant circuit which in-turn affects the resonant frequencies and the Q of the resonant circuit. Superimposed electric fields affect the flow of electrons in the field emission diode and triode components of the non-linear resonant circuit. Superimposed electric and/or magnetic fields can be static or time varying. Suitable methods for generation of superimposed magnetic field include the use magnets, electromagnets, and inductive components. Superimposed electric and magnetic fields can be uniform in space or can have spatial variation. Orientation of the superimposed electric and magnetic fields can be either constant or time varying. Suitable time varying electric and magnetic fields can be also produced by electromagnetic radiation. Such electromagnetic radiation can be AM and/or FM modulated to produce corresponding modulation of electromagnetic radiation generated by the composite dipole array.

Figure 33:
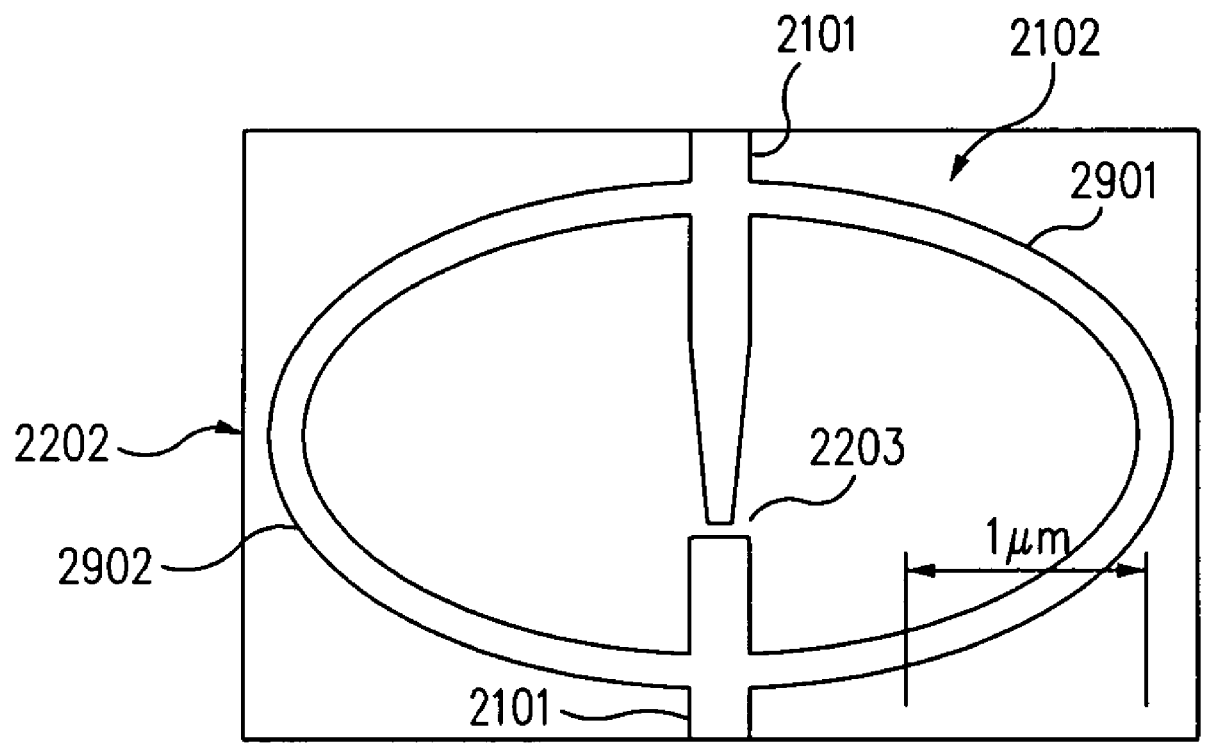
FIG. 33 shows an electromicrograph illustrating a field emission device (FED) diode and an inductor cooperating to define a non-linear resonant circuit connecting each two adjacent micro-dipoles, in accordance with an aspect of the present invention.

FIG. 33 shows a SEM picture of a fabricated device, showing an exemplary non-linear resonant circuit 2102 (similar to that of FIG. 29) having a field emission diode (FED) 2203 the diode capacitance and inductor 2202. Inductor 2202 is defined by two arc-shaped conductive paths 2901 and 2902. Those skilled in the art will appreciate that diode 2203 and/or inductor 2202 can have various different configurations, such as those shown in FIGS. 24-27 and FIGS. 28-32.

Figure 34:
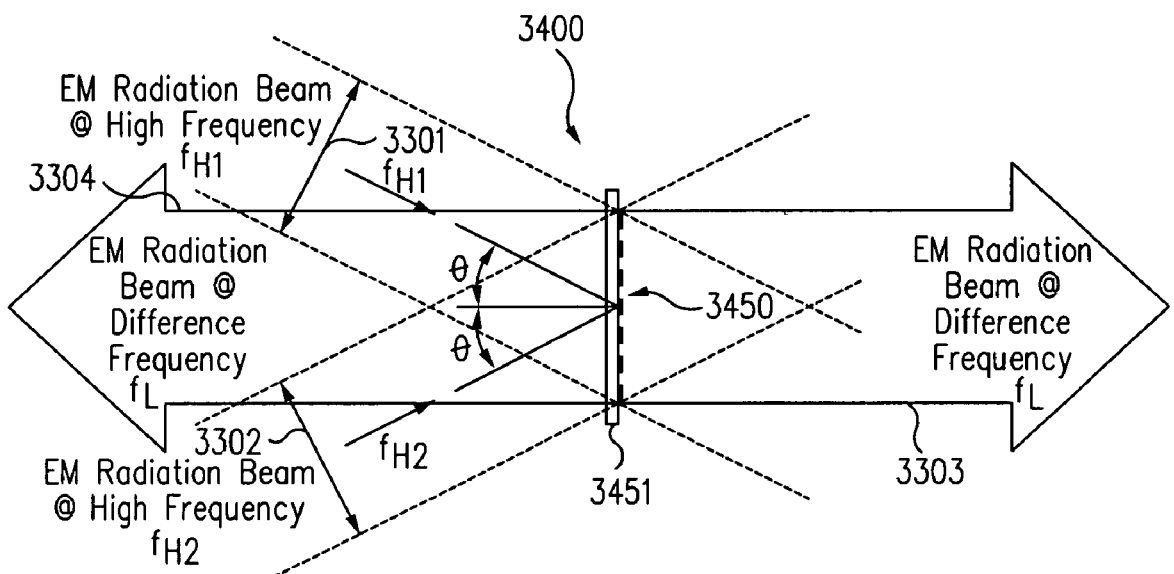
FIG. 34 shows a block diagram illustrating a difference frequency generator for providing THz radiation in accordance with an exemplary embodiment of the present invention.

FIG. 34 shows an exemplary embodiment of a difference frequency generator 3400 using a composite dipole array 3450 according to one aspect of the present invention. Composite dipole array 3450 is irradiated with electromagnetic radiation beams 3301 and 3302 having respective, closely spaced, frequencies $f_{H1}$ and $f_{H2}$. Electromagnetic radiation beams 3301 and 3302 are mutually disposed at an angle $2\theta$ with respect to each other and intersect at composite dipole array 3450. The electromagnetic radiation beams 3301 and 3302 are incident onto the surface of composite dipole array 3450 at angle $\theta$ with respect to a surface normal thereof.

The composite dipole array 3450 is designed to resonate at frequencies $f_{H1}$ and $f_{H2}$, as well as at the difference frequency $f_L = f_{H1} - f_{H2}$. In addition, the composite dipole array substrate 3451 is formed of material which is at least partially transparent to electromagnetic radiation at the frequencies $f_{H1}$, $f_{H2}$ and $f_L$. In response to irradiation by beams 3301 and 3302, composite dipole array 3450 generates electromagnetic radiation at the difference frequency $f_L$. The electromagnetic radiation at difference frequency $f_L$ propagates normal to the composite dipole array 3350 surface forming a forward beam 3303 and backward beam 3304. The forward beam 3303 can be radiated into open space. The backward beam 3304 penetrates into the composite dipole array substrate 3351. Since substrate 3351 is formed of material that is substantially transparent at the frequency $f_L$, then the backward beam 3304 will be transmitted through substrate 3351 with minimal losses. However, the substrate 3351 can include a layer of material reflective at the frequency $f_L$ and the backward beam 3304 can be reflected so that it is constructively added to forward beam 3303.

Figure 35:
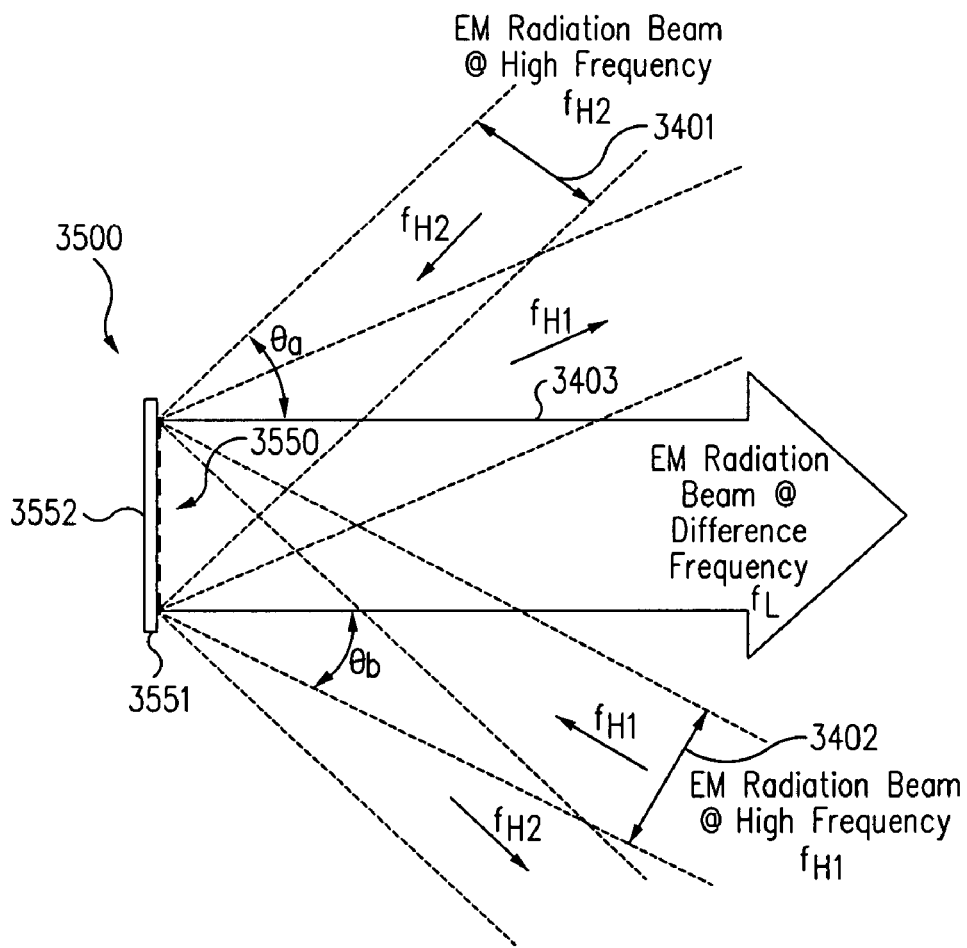
FIG. 35 shows a block diagram illustrating another difference frequency generator for providing THz radiation in accordance with an exemplary embodiment of the present invention.

FIG. 35 shows another exemplary embodiment of a difference frequency generator 3500 using a composite dipole array 3550. The composite dipole array 3550 is generally the same as the composite dipole array 3450 (FIG. 34), except that it includes a layer of material reflective at the frequencies $f_{H1}$ and $f_{H2}$, formed intermediate composite dipole array 3550 and a substrate 3551. In the difference frequency generator 3500, the two electromagnetic radiation beams 3401. and 3402 are incident on the surface of composite dipole array 3550 at angles $\theta_a$ and $\theta_b$, respectively. The difference frequency generator 3500 of FIG. 35 has two distinct advantages over the difference frequency generator 3400 of FIG. 34. First, substrate 3551 of the composite dipole array 3550 does not have to be transparent at the frequencies $f_{H1}$ and $f_{H2}$. This feature allows greater flexibility in choosing the material. Second, a back surface 3552 of substrate 3551 can be attached to a heat sink (not shown) for effective removal of waste heat from the composite dipole array 3500.

Sources of electromagnetic radiation for use with the present invention include but are not limited to lasers (e.g., $CO_2$ lasers and near infrared solid-state lasers) and radio frequency sources. Electromagnetic radiation sources can be also AM or FM modulated for the purpose of modulating the composite dipole array output. Furthermore, one or more beams from the electromagnetic radiation sources can be also spatially modulated.

The present invention provides approximately an order of magnitude of improvement with respect to contemporary systems in efficiency when generating or detecting THz radiation. Thus, according to one aspect, the present invention comprises a composite dipole array having FED diodes for use with the HFC technique for frequency conversion of electromagnetic radiation in a broad spectrum ranging from microwaves to optical frequencies.

Further, the present invention provides enhanced efficiency in the generation of electromagnetic radiation by the HFC technique; provides enhanced efficiency of receiving electromagnetic radiation by the HFC technique; enables high-average power generation of electromagnetic radiation in the sub-millimeter regime, enable high resolution imaging of sub-millimeter wavelengths electromagnetic radiation signals; facilitates the construction of a compact, lightweight, and portable THz imaging system; facilitates composite dipole array operation with sub-millimeter wavelength electromagnetic radiation; reduces parasitic capacitance in composite dipole arrays; reduces noise in composite dipole arrays; facilitates the construction of radiation hardened THz generators and detectors; and facilitates the construction of temperature insensitive THz generators and detectors.

THz electromagnetic radiation has the advantage of being able to readily penetrate many common non-conductive materials, so as to provide images or absorption spectra of the materials encountered. It also has the advantage of being non-ionizing and is therefore substantially less harmful than other radiation sources.

The present invention provides methods and systems for generating and imaging THz electromagnetic radiation for a variety of applications such as remote sensing (such as in spectroscopy applications for the standoff sensing of contraband including guns, knives, explosives, chemical agents, biological agents, and drugs), short range covert communications, spacecraft communications, process and quality control (such as in the manufacturing of chemicals and pharmaceuticals), compact radar ranging systems, force protection (CWD), radar imaging (including 3D radar), multi-spectral imaging, seeing through walls (such as for military and police surveillance/SWAT operations), search and rescue, landing aids, space imaging, non-destructive inspection, inter-satellite communication links, tactical data links (weather and dust resistant), testing integrated circuits, and even medical imaging (such as 3D tomography) and treatment.

Embodiments described above illustrate but do not limit the invention. It should also be understood that numerous modifications and variations are possible in accordance with the principles of the present invention. Accordingly, the scope of the invention is defined only by the following claims.

We claim:

1. A linear dipole array comprising:
    a plurality of dipoles arranged end-to-end and defining a generally one-dimensional linear array, wherein all of the dipoles are substantially identical; and a non-linear resonant circuit electrically interconnecting ends of corresponding adjacent dipoles throughout the linear dipole array such that a serial path is formed through all of the dipoles and the non-linear resonant circuits within the linear dipole array, wherein the linear dipole array forms a macro-dipole antenna, and wherein the dipoles are resonant at a higher frequency than a resonant frequency of the macro-dipole antenna.

2. The linear dipole array of claim 1, wherein the linear dipole array is one of a plurality of linear dipole arrays which form a composite dipole array, with the non-linear resonant circuits adapted to allow current flow serially through all of the dipoles and the non-linear resonant circuits within each of the linear dipole arrays, and wherein the linear dipole arrays are configured to be resonant at a terahertz frequency.

3. The linear dipole array of claim 1 wherein the non-linear resonant circuits couple the plurality of dipoles to facilitate current flow between the dipoles to radiate electromagnetic radiation at the resonant frequency of the macro-dipole antenna.

4. A composite dipole array comprising:
a plurality of linear dipole arrays defining a generally planar array, each of the linear dipole arrays comprising:
a plurality of dipoles defining a generally linear array, wherein all of the dipoles are substantially identical; and
a non-linear resonant circuit electrically interconnecting corresponding adjacent dipoles within the linear dipole array such that a serial path is formed through all of the dipoles and the non-linear resonant circuits within the linear dipole array, wherein each of the linear dipole arrays forms a macro-dipole antenna, and wherein the dipoles are resonant at a higher frequency than a resonant frequency of the macro-dipole antenna.

5. The composite dipole array of claim 4, wherein the individual dipoles are configured to be resonant at a frequency and the linear dipole arrays are configured to be resonant at another frequency.

6. The composite dipole array of claim 4, wherein the individual dipoles are configured to be resonant at an infrared frequency and the linear dipole arrays are configured to be resonant at a THz frequency.

7. The composite dipole array of claim 4, wherein the non-linear resonant circuits are configured to inhibit current flow between adjacent dipoles at one frequency more than they inhibit current flow between adjacent dipoles at another frequency.

8. The composite dipole array of claim 4, wherein the non-linear resonant circuit comprises a diode.

9. The composite dipole array of claim 4, wherein the non-linear resonant circuit comprises a diode and at least one of a capacitor and an inductor.

10. The composite dipole array of claim 4, wherein the non-linear resonant circuit comprises a field effect diode.

11. The composite dipole array of claim 4, wherein the non-linear resonant circuit comprises a triode.

12. The composite dipole array of claim 4, wherein:
the non-linear resonant circuit comprises a triode; and
a grid of the triode is in electrical communication with an antenna.

13. The composite dipole array of claim 4, further comprising a substrate upon which the dipoles and the nonlinear resonant circuits are formed.

14. The composite dipole array of claim 4, wherein the nonlinear resonant circuits comprise:

a diode having a gap between a cathode and an anode thereof; and
a substrate upon which the diodes are formed, the substrate having a trench formed therein proximate the gap so as to mitigate perturbation of an electrical field within the gap.

15. The composite dipole array of claim 4, further comprising:
a substrate upon which the linear dipole arrays are formed; and
an insulating layer formed intermediate the linear dipole arrays and the substrate.

16. The composite dipole array of claim 4, further comprising:
a substrate upon which the linear dipole arrays are formed; and
an insulating layer formed intermediate the linear dipole arrays, and the substrate, the insulating layer being formed of a plurality of dielectric layers.

17. The composite dipole array of claim 4, further comprising:
a substrate upon which the linear dipole arrays are formed; and
an insulating layer formed intermediate the linear dipole arrays and the substrate, the insulating layer being formed of a plurality of dielectric layers having thicknesses that enhances reflection at a predetermined frequency.

18. The composite dipole array of claim 4, further comprising:
a substrate upon which the linear dipole arrays are formed; and
an insulating layer formed intermediate the linear dipole arrays and the substrate, the insulating layer being formed of a plurality of dielectric layers having thicknesses that enhance transmission at a predetermined frequency.

19. The composite dipole array of claim 4, further comprising;
a substrate upon which the linear dipole arrays are formed; and
a reflector formed upon the substrate and configured so as to reflect electromagnetic radiation emitted from the composite dipole array in one direction such that it constructively interferes with electromagnetic radiation emitted from the composite dipole array in another direction.

20. The composite dipole array of claim 4, wherein the non-linear resonant circuit comprises a diode formed of ends of the dipoles.

21. The composite dipole array of claim 4, wherein the non-linear resonant circuit comprises a diode formed of layers of a material different from that of the dipoles proximate ends of the dipoles.

22. The composite dipole array of claim 4, wherein the non-linear resonant circuit comprises a diode formed of layers of refractory material proximate ends of the dipoles.

23. The composite dipole array of claim 4, wherein the non-linear resonant circuit comprises an inductor defined by a generally arc-shaped conductive path between a cathode and an anode of a diode of the non-linear resonant circuit.

24. The composite dipole array of claim 4, wherein the non-linear resonant circuit comprises an inductor defined by two generally arc-shaped conductive paths between a cathode and an anode of a diode of the nonlinear resonant circuit.

25. The composite dipole array of claim 4, wherein the non-linear resonant circuit comprises an inductor defined by two generally arc-shaped conductive paths between a cathode and an anode of a diode of the non-linear resonant circuit, at least one of the generally arc-shaped conductive paths having a capacitor formed therein.

26. The composite dipole array of claim 4, wherein the plurality of dipoles defining a generally linear array is configured to receive electromagnetic radiation at a first frequency and a second frequency and to re-radiate electromagnetic radiation at a third frequency.

27. The composite dipole array of claim 26, wherein the individual dipoles are configured to be resonant at the first and the second frequency and the linear dipole arrays are configured to be resonant at the third frequency.

28. The composite dipole array of claim 26, wherein the individual dipoles are configured to be resonant at infrared frequencies and the linear dipole arrays are configured to be resonant at a THz frequency.

29. The composite dipole array of claim 26, wherein the non-linear resonant circuits are configured to inhibit current flow between adjacent dipoles at the first and the second frequency more than they inhibit current flow between adjacent dipoles at the third frequency.

30. The composite dipole array of claim 4, wherein the non-linear resonant circuits couple the plurality of dipoles within each of the linear dipole arrays to facilitate current flow between the dipoles to radiate electromagnetic radiation at the resonant, frequency of the macro-dipole antenna.

31. A method for forming a linear dipole array, the method comprising forming a plurality of non-linear resonant circuits intermediate a corresponding plurality of pairs of substantially identical adjacent dipoles such that a serial path is formed through all of the dipoles and the non-linear resonant circuits within the linear dipole array, wherein the linear dipole array forms a macro-dipole antenna, and wherein the dipoles are resonant at a higher frequency than a resonant frequency of the macro-dipole antenna.

32. The method as recited in claim 31, wherein forming a non-linear resonant circuit comprises forming a field emission device.

33. The method as recited in claim 31, wherein the linear dipole array is one of a plurality of linear dipole arrays formed to provide a composite dipole array.

34. The method as recited in claim 31, wherein the nonlinear resonant circuits couple the plurality of dipoles to facilitate current flow between the dipoles to radiate electromagnetic radiation at the resonant frequency of the macro-dipole antenna.

* * * * *